US012773512B2

(12) United States Patent
Lin et al.

(10) Patent No.: US 12,773,512 B2
(45) Date of Patent: Oct. 27, 2026

(54) RETAINING DEVICE FOR MEDICAL EQUIPMENT

(71) Applicant: TZU CHI UNIVERSITY OF SCIENCE AND TECHNOLOGY, Hualien County (TW)

(72) Inventors: Zu-Chun Lin, Hualien County (TW); Hsin-Ling Hsieh, Hualien County (TW); Yi-Lin Hsieh, Hualien County (TW)

(73) Assignee: Tzu Chi University, Hualien County (TW)

( * ) Notice: Subject to any disclaimer, the term of this patent is extended or adjusted under 35 U.S.C. 154(b) by 773 days.

(21) Appl. No.: 18/307,423

(22) Filed: Apr. 26, 2023

(65) Prior Publication Data

US 2024/0358953 A1 Oct. 31, 2024

(51) Int. Cl.
*A61M 16/04* (2006.01)
*A61J 15/00* (2006.01)
*A61M 25/02* (2006.01)

(52) U.S. Cl.
CPC ...... *A61M 16/0497* (2013.01); *A61J 15/0061* (2013.01); *A61M 16/0463* (2013.01);
(Continued)

(58) Field of Classification Search
CPC .......... A61M 16/0497; A61M 16/0493; A61M 2025/0206; A61M 2025/022;
(Continued)

(56) References Cited

U.S. PATENT DOCUMENTS 3,946,742 A * 3/1976 Eross .................... A61M 25/02
128/DIG. 26
4,742,824 A * 5/1988 Payton .............. A61M 16/0666
128/207.18
(Continued)

FOREIGN PATENT DOCUMENTS

CN 202154931 U * 3/2012
CN 107233648 A * 10/2017 ........ A61M 16/0402
(Continued)

OTHER PUBLICATIONS

English translation for TW-I586390, machine translated by espacenet.com.*

*Primary Examiner* — Tu A Vo
(74) *Attorney, Agent, or Firm* — Rosenberg, Klein & Lee

(57) ABSTRACT

A retaining device for medical equipment includes a main body, a strap, and a retaining seat. The main body includes a solid portion, an open portion, and a coupling unit. The open portion corresponds in position to the mouth of a human body. The coupling unit is disposed on the solid portion. Two sides of the main body are defined as a first side and a second side relative to a longitudinal centerline, respectively. The strap is coupled to the main body. The retaining seat is detachably or rotatably coupled to the solid portion through the coupling unit. The retaining seat includes a first tube retaining portion. The first tube retaining portion corresponds in position to the open portion. A relative position between the first tube retaining portion and the open can be changed by detaching and reversing the retaining seat or rotating the retaining seat.

7 Claims, 29 Drawing Sheets

(52) U.S. Cl.
CPC ...... *A61M 16/0493* (2014.02); *A61J 15/0003* (2013.01); *A61M 2025/0206* (2013.01); *A61M 2025/022* (2013.01)

(58) Field of Classification Search
CPC .... A61M 2025/024; A61M 39/28–288; A61M 5/1418; A61M 39/1011; A61M 2039/1077; A61J 15/0061; A61J 15/0003; A61J 15/0053; A61J 15/0065; F16L 3/01
See application file for complete search history.

(56) References Cited

U.S. PATENT DOCUMENTS

| | | | | | |
|---|---|---|---|---|---|
| 5,345,931 | A * | 9/1994 | Battaglia, Jr. | A61M 25/02 604/179 |
| 5,437,273 | A * | 8/1995 | Bates | A61M 16/0488 128/207.14 |
| 5,653,232 | A * | 8/1997 | Rogers | A61M 16/0488 128/207.14 |
| 5,806,516 | A * | 9/1998 | Beattie | A61M 16/0488 128/207.14 |
| 5,934,276 | A * | 8/1999 | Fabro | A61M 25/02 128/207.14 |
| 6,067,985 | A * | 5/2000 | Islava | A61M 16/0488 128/207.14 |
| 6,634,359 | B1 * | 10/2003 | Rudy, Jr. | A61M 16/0493 128/207.14 |
| 8,726,903 | B2 * | 5/2014 | Levine | A61M 16/0497 128/207.14 |
| 2002/0151871 | A1 * | 10/2002 | Gaiser | A61M 16/0493 604/528 |
| 2011/0126839 | A1 * | 6/2011 | Levine | A61M 16/0497 128/207.14 |
| 2012/0168571 | A1 * | 7/2012 | Bond | A61M 25/02 248/70 |
| 2014/0261463 | A1 * | 9/2014 | Visconti | A61B 1/00154 128/861 |
| 2016/0339194 | A1 * | 11/2016 | Molden | A61M 16/0497 |
| 2021/0187229 | A1 * | 6/2021 | Brar | A61M 16/0493 |
| 2022/0023608 | A1 * | 1/2022 | Johnson | A61M 39/1011 |

FOREIGN PATENT DOCUMENTS

| | | | | | |
|---|---|---|---|---|---|
| CN | 107929903 | A | * | 4/2018 | A61M 16/0493 |
| CN | 110585028 | A | * | 12/2019 | A61J 15/0061 |
| CN | 211536145 | U | * | 9/2020 | |
| CN | 113769236 | A | * | 12/2021 | A61M 25/02 |
| CN | 214970652 | U | * | 12/2021 | |
| KR | 20140103546 | A | * | 8/2014 | A61M 16/0694 |
| TW | I586390 | B | * | 6/2017 | |
| TW | 201806639 | A | | 3/2018 | |

* cited by examiner

RETAINING DEVICE FOR MEDICAL EQUIPMENT

FIELD OF THE INVENTION

The present invention relates to a retaining device for medical equipment, and more particularly to a retaining device that is detachably or rotatably coupled to a main body through a coupling unit, so as to retain medical equipment, such as an endotracheal tube, a nasogastric tube, an orogastric tube or a bite block. It is easy to change the position of the endotracheal tube or the bite block, meeting the needs of clinical care.

BACKGROUND OF THE INVENTION

Referring to FIG. 20, when a patient is unconscious or loses upper respiratory tract reflexes, it is required to insert an endotracheal tube 10 into the trachea of the human body via the oral cavity, and then the endotracheal tube 10 is connected to a ventilator outside the human body for first aid. For the patient inserted with the endotracheal tube 10, it is necessary to use a nasogastric tube 20 to be inserted from the patient's nose through the throat to the stomach. The nasogastric tube 20 is used for tube-feeding, so as to provide nourishment essential for growth and the maintenance of life. In order to prevent some restless patients from biting the endotracheal tube 10 to obstruct the gas flow, the patient may bite a bite block 30 to open the mouth. In order to retain the foregoing medical equipment in the correct position, in general, an adhesive tape is used for retaining the foregoing medical equipment. When the nurse or caregiver intends to replace medical equipment or clean the oral cavity of the patient, such as brushing teeth, the adhesive tape needs to be torn off. After replacing the medical equipment or cleaning the oral cavity, the adhesive tape is used again for retaining the medical equipment. Sticking and tearing off the adhesive tape frequently may cause damage to the patient's skin.

In order to solve the above-mentioned problem of retaining medical equipment for the mouth and nose, Taiwan Patent No. I678215 discloses a composite functional tube, comprising a main body, a tenon, and a strap. A tube groove is disposed around the main body. Two sides of the main body have an engaging groove and a notch. The main body includes a positioning seat. The positioning seat has a tube positioning groove and a tenon positioning groove. The tenon is movably disposed under the main body and the positioning seat. Two ends of the strap are coupled to the main body. With the strap secured to the human body, the tube is first retained in the engaging groove and passes through the surface of the main body to be inserted through the notch. Then, the tube is wound in the tube groove. The tenon is pushed to pressurize the tube for the internal passage to be in a closed state, thereby preventing the fluid in the tube from flowing out (such as gastrointestinal fluid), and one end of the tube is retained in the tube positioning groove.

Although the above-mentioned composite functional tube device can retain the tube conveniently and solve the problems existing in the use of adhesive tape, it is still unable to retain the bite block, change the position of retaining the tube, observe the state of the oral cavity, and perform oral cleaning.

SUMMARY OF THE INVENTION

According to one aspect of the present invention, a retaining device for medical equipment is provided. The retaining device is used for retaining an endotracheal tube. The retaining device comprises a main body, a strap, and a retaining seat. The main body includes a solid portion, an open portion, and a coupling unit. The open portion corresponds in position to the mouth of a human body. The coupling unit is disposed on the solid portion. Two sides of the main body are defined as a first side and a second side relative to a longitudinal centerline, respectively. The strap is coupled to the main body. The retaining seat is detachably or rotatably coupled to the solid portion through the coupling unit. The retaining seat includes a first tube retaining portion. The first tube retaining portion corresponds in position to the open portion. A relative position between the first tube retaining portion and the open can be changed by detaching and reversing the retaining seat or rotating the retaining seat.

Preferably, the coupling unit is located at a position where the longitudinal centerline passes, and the first tube retaining portion deviates from the longitudinal centerline.

Preferably, the retaining seat further includes a bite block holder. The first tube retaining portion and the bite block holder are arranged along a transverse direction.

Preferably, the retaining seat includes a first face and a second face opposite to the first face. The bite block holder includes an opening and a stopper. The stopper includes a first clamp plate. A first holding groove is formed between the first clamp plate and the first face. The first clamp plate corresponds in shape to a notch of a bite block.

Preferably, the first clamp plate is formed on one end of the stopper. The stopper passes through and is movable on the retaining seat. The stopper further includes a second clamp plate on another end thereof. A second holding groove is selectively formed between the second clamp plate and the second face. The second clamp plate corresponds in shape to the notch of the bite block.

Preferably, the retaining seat further includes a second tube retaining portion. The first tube retaining portion, the bite block holder and the second tube retaining portion are arranged along the transverse direction.

Preferably, the coupling unit includes a movable cap and a protruding shaft. The retaining seat has a through hole. The retaining seat is sleeved on the protruding shaft via the through hole. The movable cap is coupled to the protruding shaft to form an unlocking position and a locking position. When in the unlocking position, the retaining seat is detachable to be reversed or rotatable relative to the main body.

Preferably, the main body further includes a main body first tube retaining portion and/or a main body third tube retaining portion. The main body first tube retaining portion and the main body third tube retaining portion are located on the first side.

Preferably, the main body further includes a main body second tube retaining portion and/or a main body fourth tube retaining portion. The main body second tube retaining portion and the main body fourth tube retaining portion are located on the second side.

Preferably, the main body first tube retaining portion includes two first protruding posts each having a first enlarged end. A spacing between the two first enlarged ends is less than a spacing between the two first protruding posts. The main body third tube retaining portion includes two third protruding posts each having a third enlarged end. A spacing between the two third enlarged ends is less than a spacing between the two third protruding posts.

Preferably, the main body second tube retaining portion includes two second protruding posts each having a second enlarged end. A spacing between the two second enlarged ends is less than a spacing between the two second protruding posts. The main body fourth tube retaining portion includes two fourth protruding posts each having a fourth enlarged end. A spacing between the two fourth enlarged ends is less than a spacing between the two fourth protruding posts.

Preferably, the retaining seat further includes a first face. The bite block holder includes an opening. The movable cap has an inner end face and a collar protruding from the inner end face. When in the locking position, the first face, the collar and the inner end face jointly define a first holding groove. The retaining device further comprises a bite block. The bite block includes a bite portion and a holding portion surrounding the around bite portion. The holding portion has a thickness corresponding to a groove width of the first holding groove. The holding portion has a notch. The notch corresponds in shape to a part of a periphery of the movable cap. When the bite portion is inserted into the opening, the notch is aligned with the position of the periphery of the movable cap, the holding portion passes through the movable cap and abuts against the first face, and the holding portion is rotated to be engaged in the first holding groove.

According to another aspect of the present invention, a retaining device for medical equipment is provided. The retaining device is used for retaining a bite block. The retaining device comprises a main body, a strap, and a retaining seat. The main body includes a solid portion, an open portion, and a coupling unit. The open portion corresponds in position to the mouth of a human body. The coupling unit is disposed on the solid portion. Two sides of the main body are defined as a first side and a second side relative to a longitudinal centerline, respectively. The strap is coupled to the main body. The retaining seat is detachably or rotatably coupled to the solid portion through the coupling unit. The retaining seat includes a bite block holder. The bite block holder corresponds in position to the open portion. A relative position between the bite block holder and the open can be changed by detaching and reversing the retaining seat or rotating the retaining seat.

Preferably, the coupling unit is located at a position where the longitudinal centerline passes, and the bite block holder deviates from the longitudinal centerline.

Preferably, the retaining seat includes a first face and a second face opposite to the first face. The bite block holder includes an opening and a stopper. The stopper includes a first clamp plate. A first holding groove is formed between the first clamp plate and the first face. The first clamp plate corresponds in shape to a notch of a bite block.

Preferably, the first clamp plate is formed on one end of the stopper. The stopper passes through and is movable on the retaining seat. The stopper further includes a second clamp plate on another end thereof. A second holding groove is selectively formed between the second clamp plate and the second face. The second clamp plate corresponds in shape to the notch of the bite block.

Preferably, the coupling unit includes a movable cap and a protruding shaft. The retaining seat has a through hole. The retaining seat is sleeved on the protruding shaft via the through hole. The movable cap is coupled to the protruding shaft to form an unlocking position and a locking position. When in the unlocking position, the retaining seat is detachable to be reversed or rotatable relative to the main body.

Preferably, the main body further includes a main body first tube retaining portion and/or a main body third tube retaining portion. The main body first tube retaining portion and the main body third tube retaining portion are located on the first side.

Preferably, the main body further includes a main body second tube retaining portion and/or a main body fourth tube retaining portion. The main body second tube retaining portion and the main body fourth tube retaining portion are located on the second side.

Preferably, the main body first tube retaining portion includes two first protruding posts each having a first enlarged end. A spacing between the two first enlarged ends is less than a spacing between the two first protruding posts. The main body third tube retaining portion includes two third protruding posts each having a third enlarged end. A spacing between the two third enlarged ends is less than a spacing between the two third protruding posts.

Preferably, the main body second tube retaining portion includes two second protruding posts each having a second enlarged end. A spacing between the two second enlarged ends is less than a spacing between the two second protruding posts. The main body fourth tube retaining portion includes two fourth protruding posts each having a fourth enlarged end. A spacing between the two fourth enlarged ends is less than a spacing between the two fourth protruding posts.

Preferably, the retaining seat further includes a first face. The bite block holder includes an opening. The movable cap has an inner end face and a collar protruding from the inner end face. When in the locking position, the first face, the collar and the inner end face jointly define a first holding groove. The retaining device further comprises a bite block. The bite block includes a bite portion and a holding portion surrounding the around bite portion. The holding portion has a thickness corresponding to a groove width of the first holding groove. The holding portion has a notch. The notch corresponds in shape to a part of a periphery of the movable cap. When the bite portion is inserted into the opening, the notch is aligned with the position of the periphery of the movable cap, the holding portion passes through the movable cap and abuts against the first face, and the holding portion is rotated to be engaged in the first holding groove.

According to the above-mentioned technical features, the present invention can achieve the following effects:

1. It is convenient to retain the endotracheal tube. The relative position between the first tube retaining portion and the open portion can be changed by detaching or rotating the retaining seat. When the endotracheal tube is inserted in the trachea from the left side of the mouth or the right side of the mouth, it can be retained properly by the first tube retaining portion.

2. The main body has the U-shaped open portion. When in use, the open portion corresponds to the patient's mouth. By moving the retaining seat, the nurse can suck the expectoration in the oral cavity for the patient. It is especially suitable for patients who need frequent sputum suction. Besides, the U-shaped open portion will not hinder the toothbrush from extending into the oral cavity. It is convenient to brush teeth for the patient. In addition, the position of the endotracheal tube in the oral cavity can be changed by moving the retaining seat, so as to prevent the endotracheal tube from causing ulceration of the oral cavity.

3. As to the bite block holder of the present invention, the bite block can be inserted in the bite block holder in an outside-in direction, without detaching the bite block holder. The bite block can be inserted in the mouth with ease, and the bite block can be retained quickly and firmly.

4. By the stopper passing through and being movable on the retaining seat, the first holding groove is formed between the first clamp plate and the first face or the second holding groove is formed between the second clamp plate and the second face for retaining the bite block, saving the installation volume of the stopper. Besides, the stopper will not protrude and press the patient's lips.

5. It is more convenient to change the position of retaining the tube via the selection of multiple retaining positions, such as the first tube retaining portion and the second tube retaining portion.

6. The fastener used for retaining the endotracheal tube is connected to the base via a thin film, so it will not fall off. The fastener will not fall into the patient's mouth.

7. The main body first tube retaining portion and the main body second tube retaining portion are respectively located on the upper section of the first side and the upper section of the second side of the main body, used for retaining the nasogastric tube. The nasogastric tube can be retained properly when it is inserted via the left nostril or the right nostril. It is convenient to perform pouring medicine, tube-feeding and drainage via the nasogastric tube in clinical practice.

8. The main body third tube retaining portion and the main body fourth tube retaining portion are respectively located on the lower section of the first side and the lower section of the second side of the main body, used for retaining the orogastric tube. The orogastric tube can be retained properly when it is inserted from the left side of the mouth or from the right side of the mouth. It is convenient to perform pouring medicine, tube-feeding and drainage via the nasogastric tube in clinical practice.

9. The bite block can be held by the first holding groove formed between the movable cap and the retaining seat, without using the stopper.

DETAILED DESCRIPTION OF THE PREFERRED EMBODIMENTS

Figure 1:
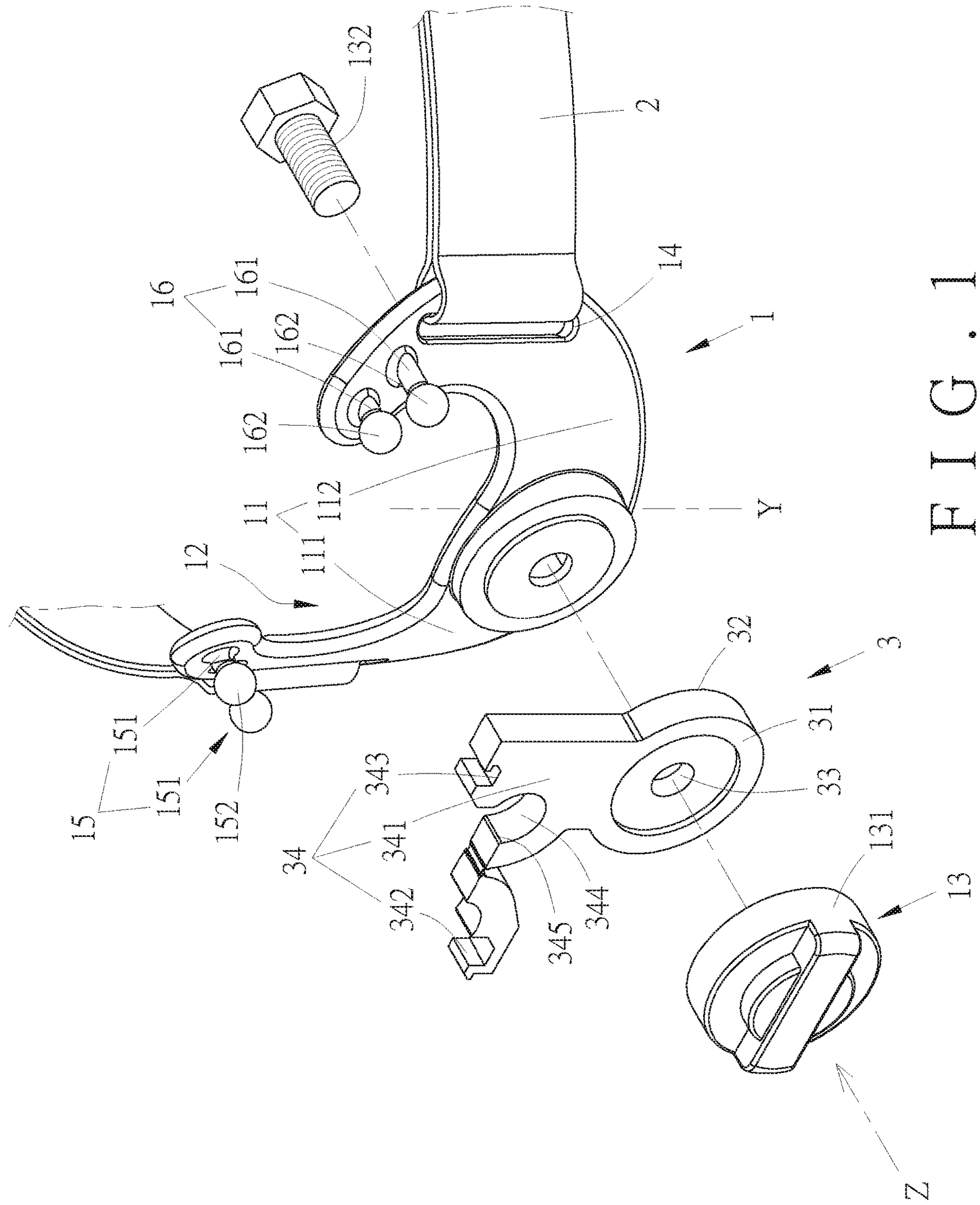
FIG. 1 is an exploded view of the retaining device for medical equipment according to a first embodiment of the present invention.

Embodiments of the present invention will now be described, by way of example only, with reference to the accompanying drawings.

The present invention discloses a retaining device for medical equipment. The retaining device may be used for retaining the following medical equipment.

1. The retaining device is used for retaining an endotracheal tube.

2. The retaining device is used for retaining an endotracheal tube, a nasogastric tube or an orogastric tube.

3. The retaining device is used for retaining an endotracheal tube, a nasogastric tube, an orogastric tube or a bite block.

4. The retaining device is used for retaining a bite block.

In addition to retaining the above-mentioned medical equipment, the present invention is beneficial to perform sputum suction, brushing teeth and other oral care when the patient is wearing the retaining device.

In the following embodiments of the present invention, the same components are denoted with the same reference numbers in the drawings.

Figure 2:
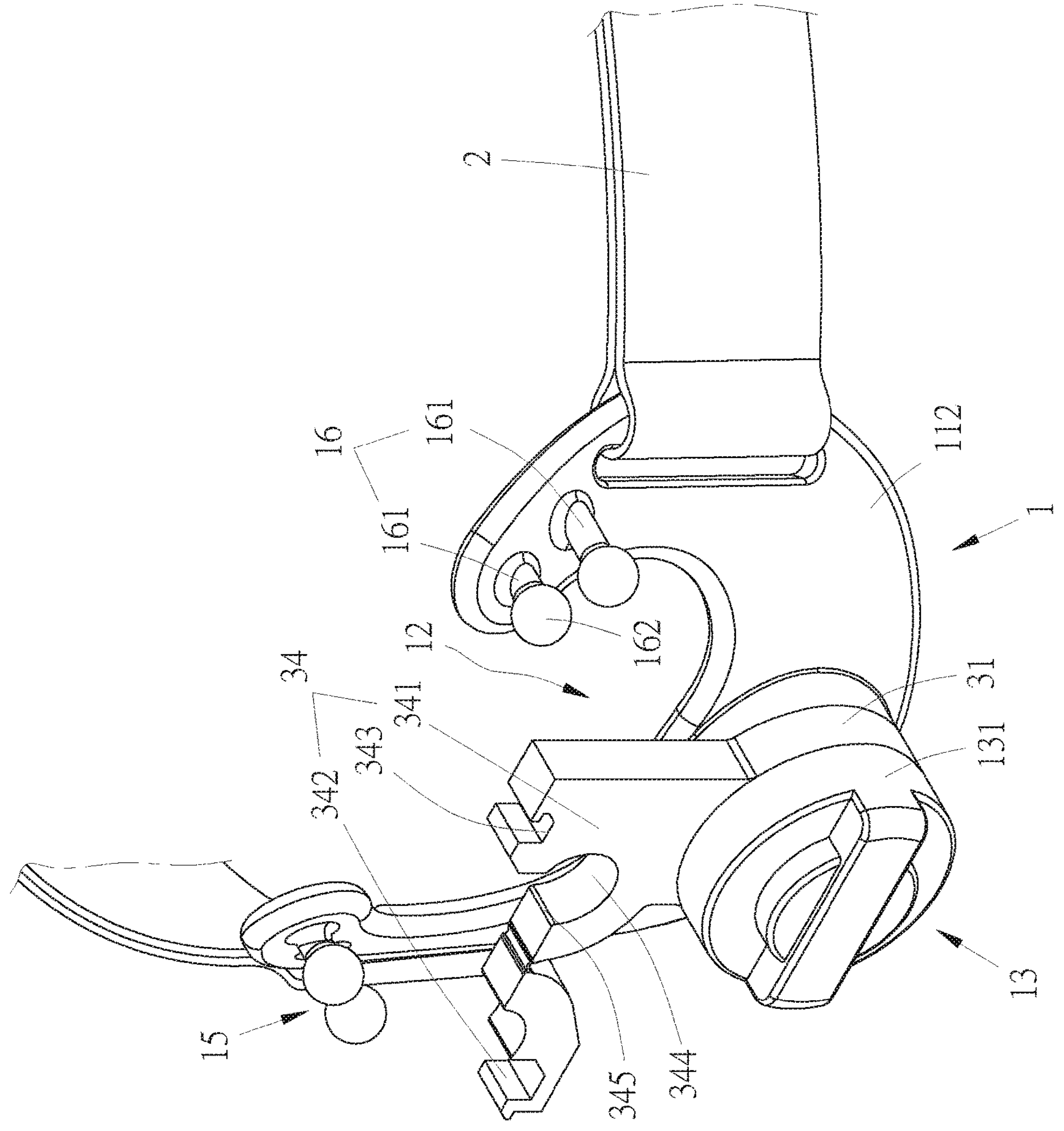
FIG. 2 is a perspective view of the first embodiment.
Figure 3:
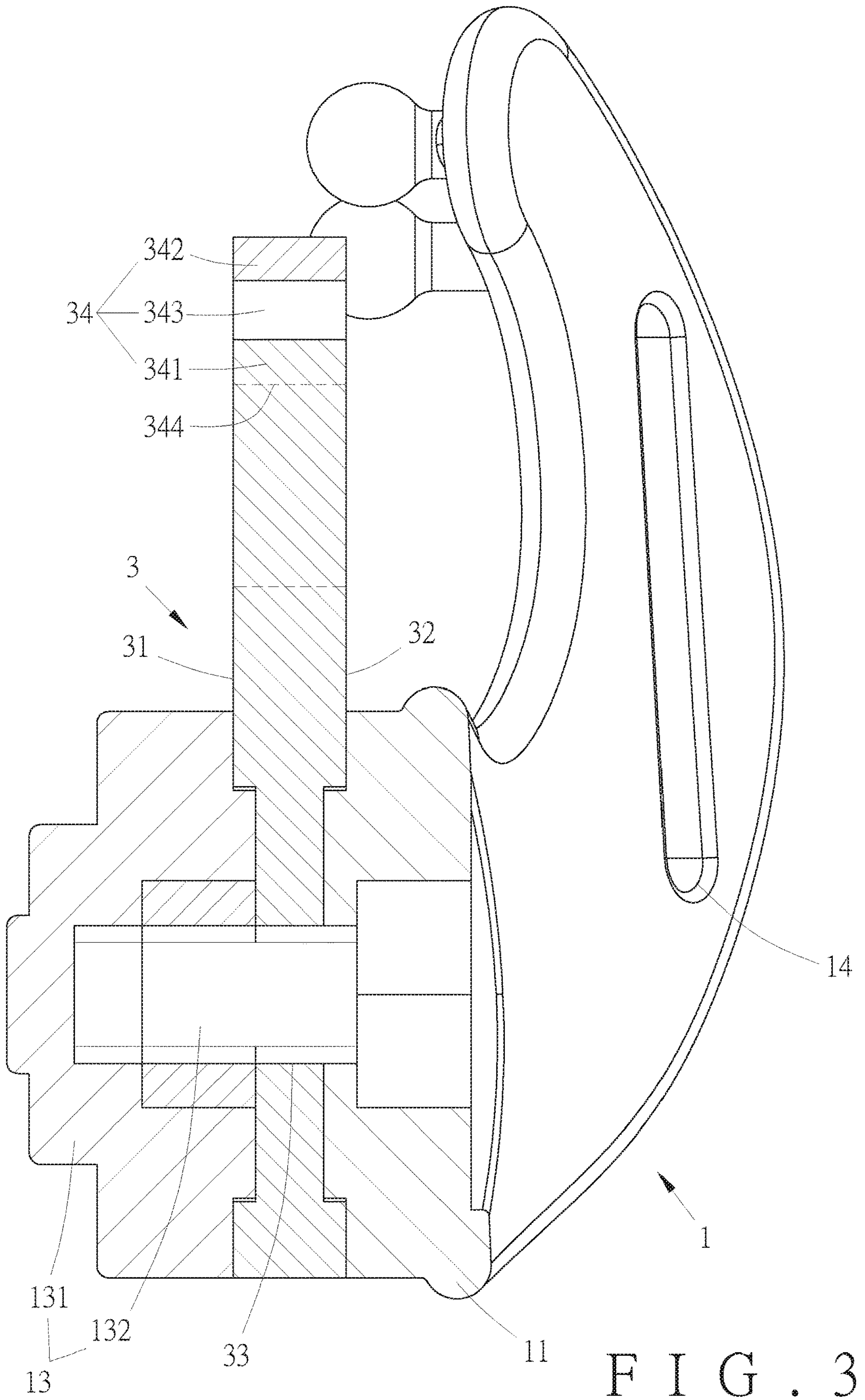
FIG. 3 is a sectional view of the first embodiment, illustrating the connection of the main body and the retaining seat.

Referring to FIG. 1 to FIG. 3, a first embodiment of the retaining device for medical equipment of the present invention is mainly used for retaining an endotracheal tube, so as to facilitate sputum suction. The retaining device for medical equipment may be further used for retaining a nasogastric tube or an orogastric tube. The retaining device for medical equipment comprises a main body 1, a strap 2, and a retaining seat 3.

The main body 1 includes a solid portion 11, an open portion 12, and a coupling unit 13. The solid portion 11 is substantially in a U shape. Two sides of the solid portion 11 of the main body 1 are defined as a first side 111 and a second side 112 relative to a longitudinal centerline Y (FIG. 4), respectively. The first side 111 and the second side 112 of the solid portion 11 each have a strap groove 14. The open portion 12 is a substantially U-shaped opening of the solid portion 11. When in use, the solid portion 11 corresponds in position to the chin of the human body, and the open portion 12 corresponds in position to the mouth of the human body. Furthermore, the solid portion 11 is curved in an insertion direction Z of the endotracheal tube 10 (FIG. 4), so that the solid portion 11 fits the chin of the human body better. The coupling unit 13 is disposed on the solid portion 11, and includes a movable cap 131 and a protruding shaft 132. In a preferred embodiment, the coupling unit 13 is located at a position where the longitudinal centerline Y passes. The movable cap 131 is detachably connected to the protruding shaft 132. In this embodiment, a threaded hole is formed in the movable cap 131. A lug is formed on the outside of the movable cap 131, which is beneficial for the user to hold and rotate the movable cap 131. The protruding shaft 132 is in the form of a bolt. The protruding shaft 132 is screwed to the threaded hole of the movable cap 131.

The strap 2 is connected to the strap grooves 14 of the main body 1.

The retaining seat 3 includes a first face 31, a second face 32, a through hole 33, and a first tube retaining portion 34. The second face 32 is opposite to the first face 31. The retaining seat 3 is detachable to be reversed, or is rotatably coupled to the solid portion 11 through the coupling unit 13. The relative position between the first tube retaining portion 34 and the open portion 12 can be changed by moving or reversing the retaining seat 3. The retaining seat 3 is sleeved on the protruding shaft 132 via the through hole 33. The movable cap 131 is coupled to the protruding shaft 132 to form an unlocking position and a locking position. When in the unlocking position, the movable cap 131 is not screwed tightly to the protruding shaft 132, so that the retaining seat 3 is rotatable relative to the main body 1 with the protruding shaft 132 as the axis. At this time, the second face 32 of the retaining seat 3 is attached to the main body 1. Another state in the unlocking position is that the movable cap 131 is fully rotated away from the protruding shaft 132. At this time, the retaining seat 3 is detached from the protruding shaft 132 and reversed 180 degrees for the first face 31 to be attached to the main body 1, thereby changing the relative position between the retaining seat 3 and the main body 1. In the locking position, the movable cap 131 and the protruding shaft 132 are in a locking state, and the retaining seat 3 is tightened and positioned between the movable cap 131 and the solid portion 11, such that the retaining seat 3 is secured to the main body 1. The first tube retaining portion 34 of the retaining seat 3 corresponds in position to the open portion 12. The first tube retaining portion 34 deviates from the longitudinal centerline Y and is located at the left side of the longitudinal centerline Y. The left side is defined according to the schematic position in FIG. 1, and is only used for orientation reference, not to define the scope of the patent. In the embodiments of the present invention, the left side corresponds to the aforementioned first side 111. The first tube retaining portion 34 includes a base 341, a fastener 342 and a fastener groove 343. The base 341 defines a retaining hole 344 and forms a positioning notch 345. The retaining hole 344 communicates with the positioning notch 345. The fastener 342 is connected to the base 341 via a thin film. The fastener 342 is rotatable to be engaged in the fastener groove 343 to close the positioning notch 345, so that the retaining hole 344 is in a completely closed state.

The main body 1 further includes a main body first tube retaining portion 15 and a main body second tube retaining portion 16. The main body first tube retaining portion 15 is located on the first side 111, preferably, on the upper section of the first side 111. The main body first tube retaining portion 15 includes two first protruding posts 151 each having a first enlarged end 152. The spacing between the two first enlarged ends 152 is less than the spacing between the two first protruding posts 151. The main body second tube retaining portion 16 is located on the second side 112, preferably, on the upper section of the second side 112. The main body second tube retaining portion 16 includes two second protruding posts 161 each having a second enlarged end 162. The spacing between the two second enlarged ends 162 is less than the spacing between the two second protruding posts 161. The upper section and the lower section mentioned in the embodiments of the present invention are defined according to the schematic positions in FIG. 1, and are only used for orientation reference, not for defining the scope of the patent.

In a preferred embodiment, the material of the base 341 having the retaining hole 344 is an elastic material, and the material of the main body first tube retaining portion 15 and the main body second tube retaining portion 16 is also an elastic material, so as to retain medical equipment with a slightly changed caliber, such as an endotracheal tube.

Figure 4:
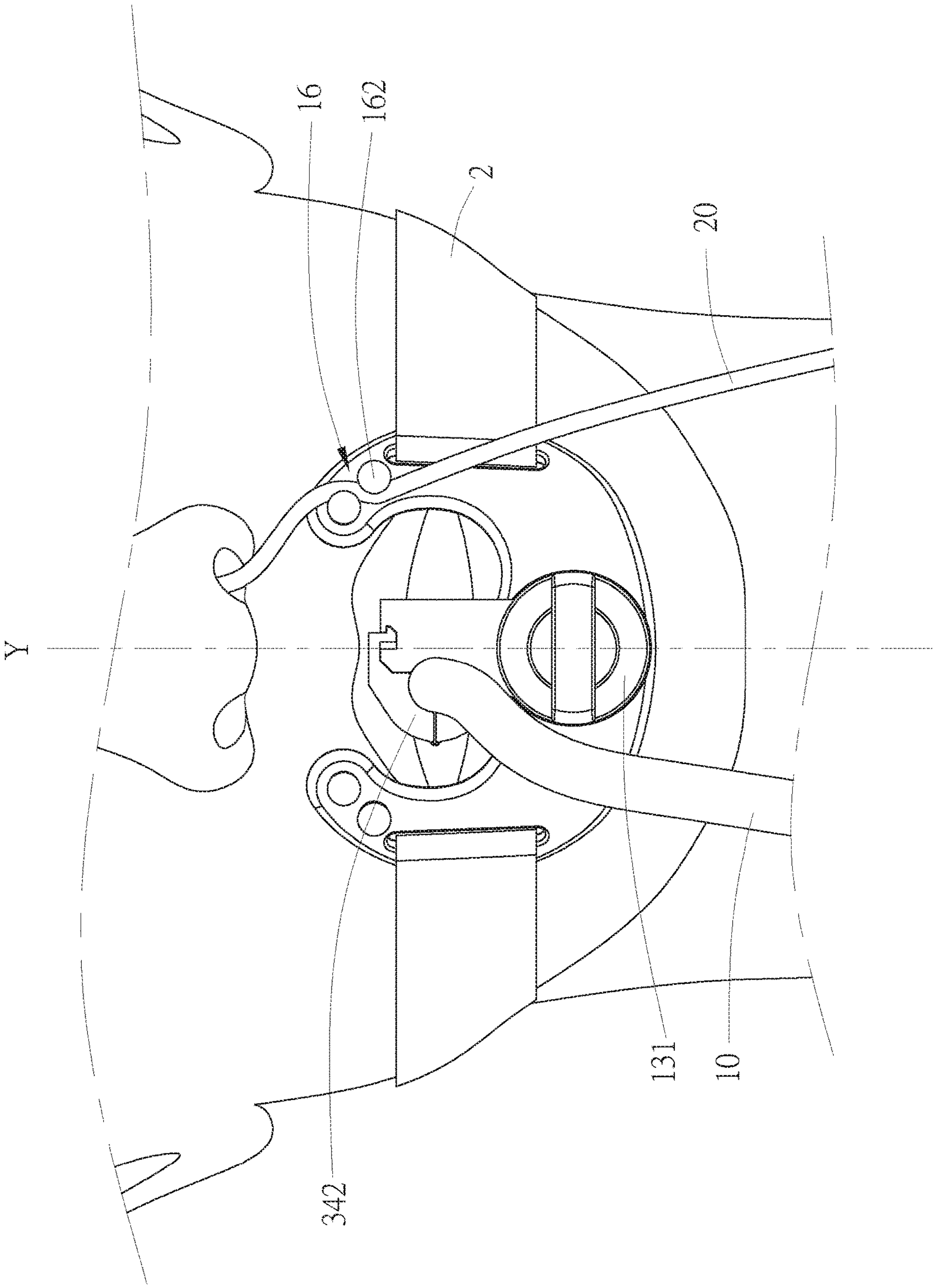
FIG. 4 is a schematic view of the first embodiment used for retaining the endotracheal tube and the nasogastric tube.

Referring to FIG. 1 and FIG. 4, when it is necessary to retain the endotracheal tube 10, the retaining device for medical equipment is used, corresponding in position to the mouth of the human body. The strap 2 is sleeved on the head of the human body for the retaining device to be secured at a position corresponding to the nose and mouth of the human body, instead of using adhesive tape. Next, the endotracheal tube 10 is placed into the retaining hole 344 from the positioning notch 345, and the fastener 342 is engaged in the fastener groove 343 to retain the endotracheal tube 10 in the retaining hole 344. Because the fastener 342 can be engaged in or disengaged from the fastener groove 343 easily, it is easy to retain the endotracheal tube 10.

When it is necessary to retain a nasogastric tube 20, the nasogastric tube 20 extending out from the nostril of the human body is selectively retained by the main body first tube retaining portion 15 or the main body second tube retaining portion 16. In this embodiment, the nasogastric tube 20 is located in the right nostril of FIG. 4, and the nasogastric tube 20 is retained by the main body second tube retaining portion 16. The nasogastric tube 20 is directly pressed in the spacing between the two second enlarged ends 162, so that the nasogastric tube 20 is retained in the spacing between the two second protruding posts 161. It is not easy to pull the retained nasogastric tube 20 accidentally, which can reduce the patient's discomfort. It is convenient to perform pouring medicine, tube-feeding and drainage for patients.

Figure 1A:
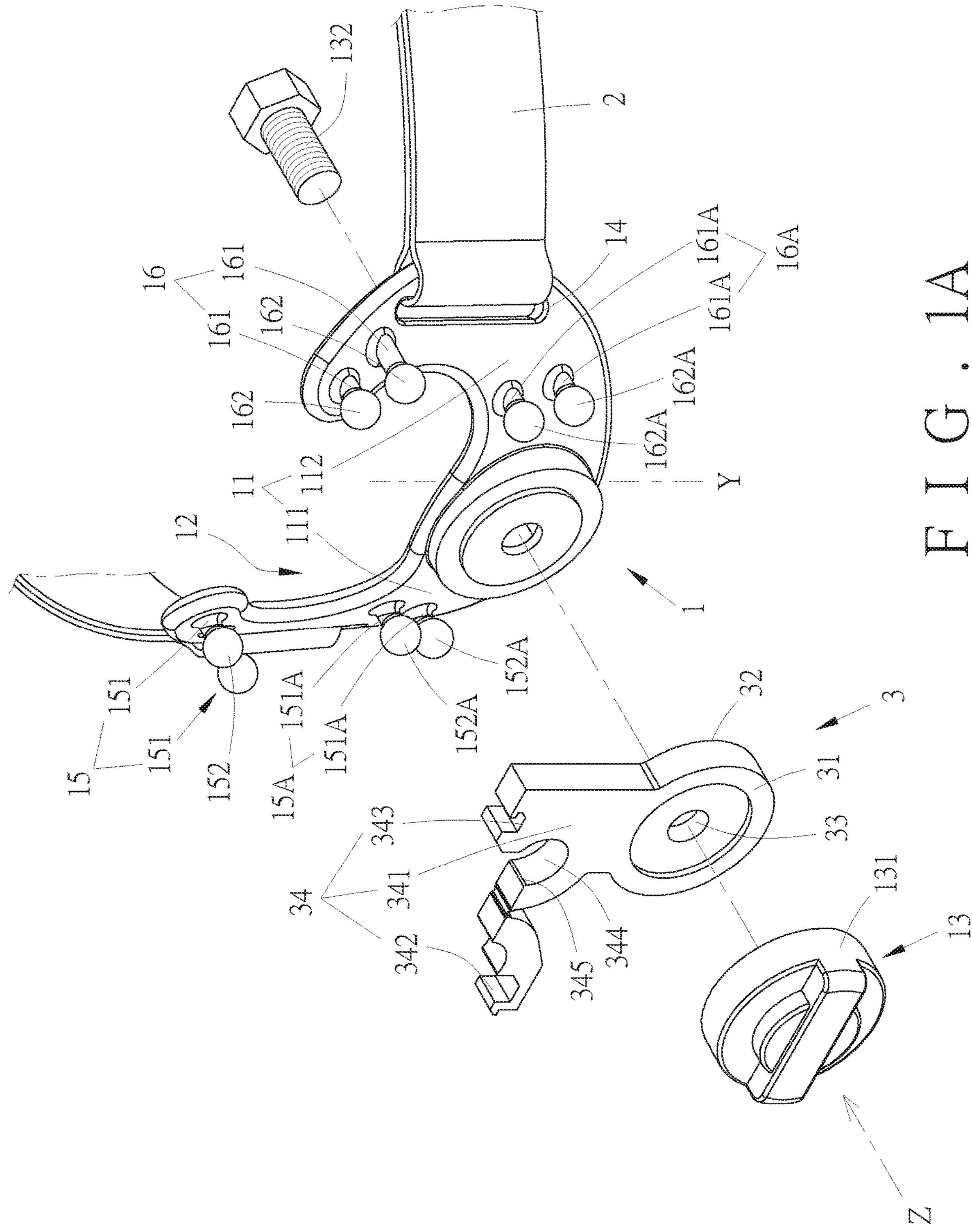
FIG. 1A is another exploded view of the retaining device for medical equipment according to the first embodiment of the present invention, wherein the main body further includes the main body third tube retaining portion and the main body fourth tube retaining portion.
Figure 4A:
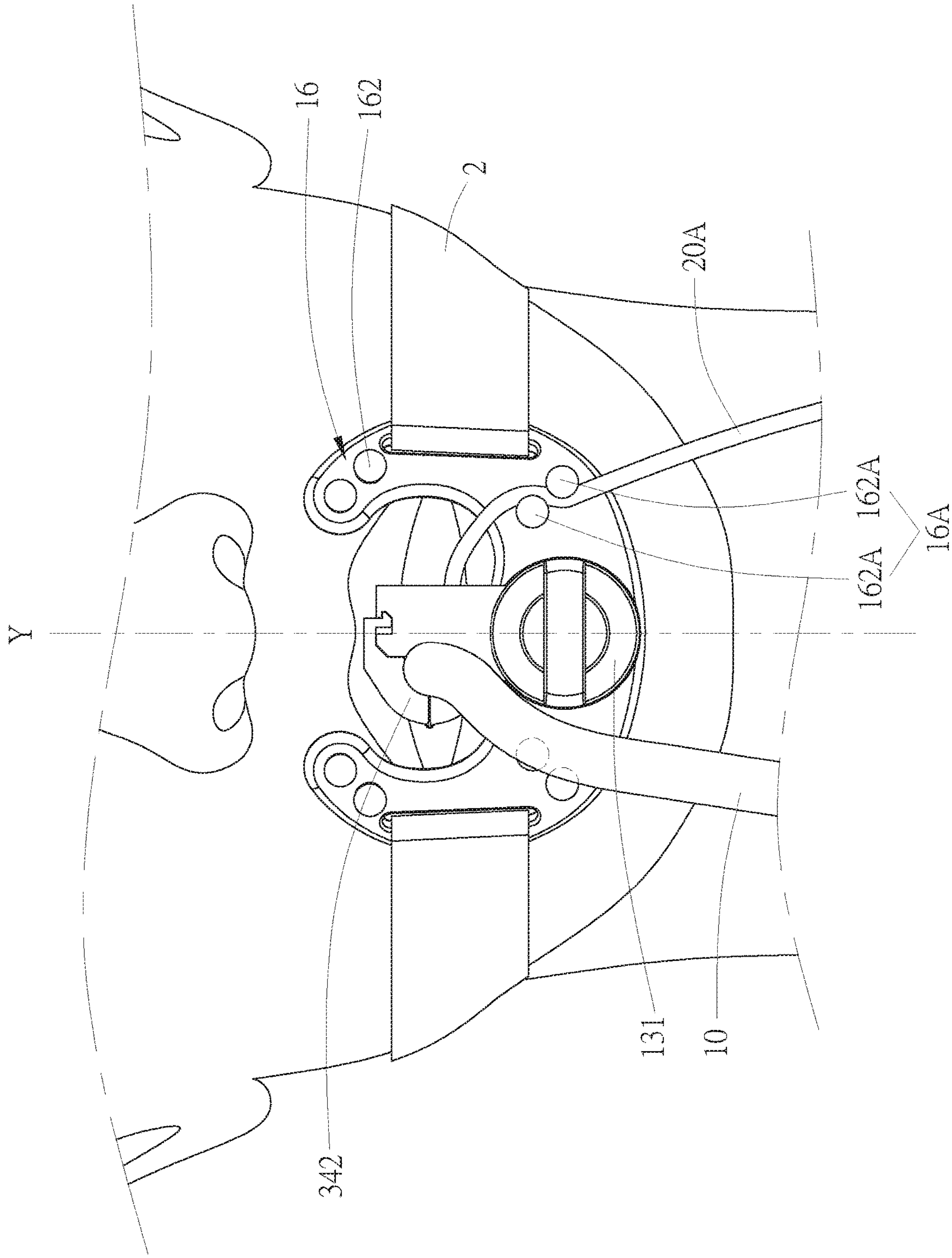
FIG. 4A is a schematic view of the first embodiment used for retaining the endotracheal tube and the orogastric tube.

Referring to the FIG. 1A and FIG. 4A, the present invention may be used for retaining an orogastric tube 20A. The main body 1 further includes a main body third tube retaining portion 15A and a main body fourth tube retaining portion 16A. The main body third tube retaining portion 15A is located on the lower section of the first side 111. The main body third tube retaining portion 15A includes two third protruding posts 151A each having a third enlarged end 152A. The spacing between the two third enlarged ends 152A is less than the spacing between the two third protruding posts 151A. The main body fourth tube retaining portion 16A is located on the lower section of the second side 112. The main body fourth tube retaining portion 16A includes two fourth protruding posts 161A each having a fourth enlarged end 162A. The spacing between the two fourth enlarged ends 162A is less than the spacing between the two fourth protruding posts 161A. The orogastric tube 20A may be retained by the main body third tube retaining portion 15A and the main body fourth tube retaining portion 16A. As shown in FIG. 4A, the orogastric tube 20A is retained by the main body fourth tube retaining portion 16A. The orogastric tube 20A enters the oral cavity from the right side of the longitudinal centerline Y. The foregoing lower section and the right side are defined according to the schematic positions in FIG. 1A, and are only used for orientation reference, not for defining the scope of the patent. Similarly, it is not easy to pull the retained orogastric tube 20A accidentally, which can reduce the patient's discomfort. It is convenient to perform pouring medicine, tube-feeding and drainage for patients.

Figure 5:
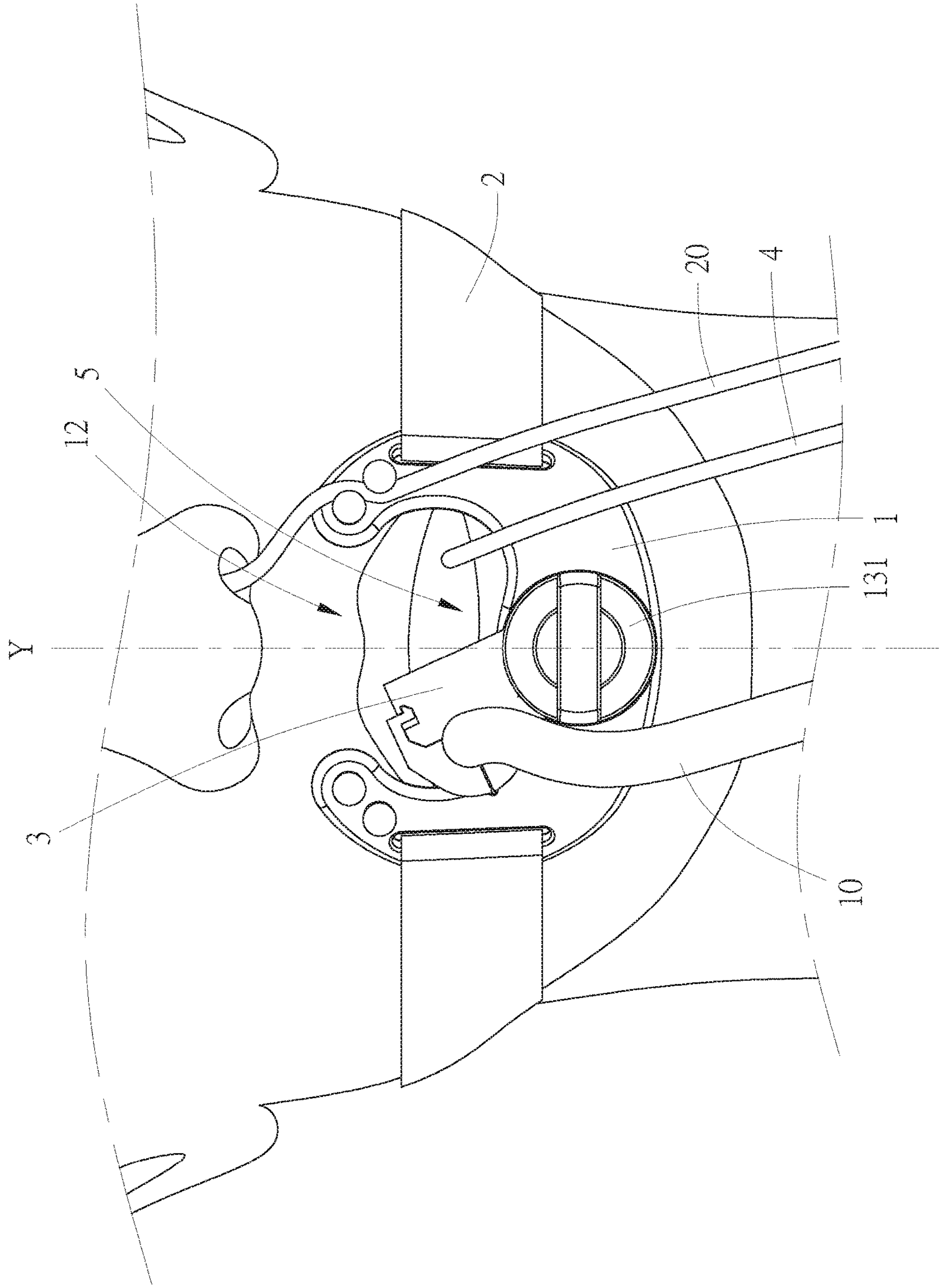
FIG. 5 is a first schematic view of the first embodiment used for performing sputum suction.
Figure 6:
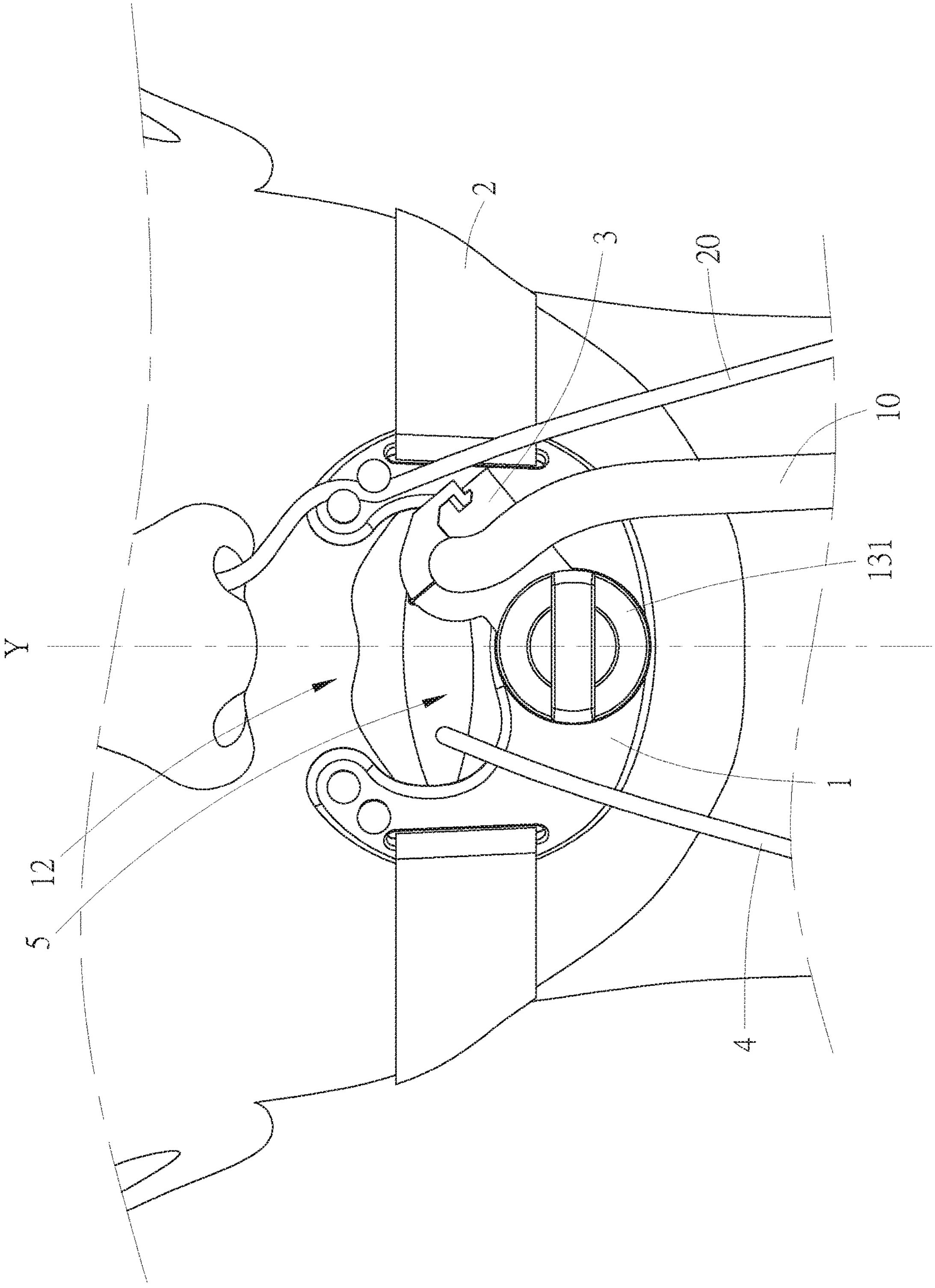
FIG. 6 is a second schematic view of the first embodiment used for performing sputum suction.

Referring to FIG. 5, when it is necessary to suck sputum for the patient, the ventilator tube at the outer end of the endotracheal tube 10 is removed first. Then, the sputum suction tube is inserted through the outer end of the endotracheal tube 10, and the sputum suction of the lungs and respiratory tract is performed via the endotracheal tube 10. Since the patient may have some expectoration remaining in the oral cavity, after the sputum is sucked via the endotracheal tube 10, the expectoration is then sucked from the oral cavity of the patient. When it is necessary to suck the expectoration in the oral cavity, the movable cap 131 is unscrewed to be in the unlocking position, and the retaining seat 3 is rotated relative to the main body 1. For example, the sputum suction tube 4 is inserted in the oral cavity 5 of the patient from the right side of the longitudinal centerline Y. When it is necessary to suck the expectoration in the oral cavity 5 for the patient, the retaining seat 3 is rotated to the left and then retained. The retaining seat 3 does not block the space of the right side of the open portion 12, so that the operation of sucking expectoration in the oral cavity 5 can be done smoothly. Referring to FIG. 6, the sputum suction tube 4 is inserted in the oral cavity 5 of the patient from the left side of the longitudinal centerline Y. When it is necessary to suck the expectoration in the oral cavity 5 for the patient, the retaining seat 3 is rotated to the right and then retained. The retaining seat 3 does not block the space of the left side of the open portion 12, so that the operation of sucking expectoration in the oral cavity 5 can be done smoothly. Sputum suction needs to be performed hourly for some patients. For frequent sputum suction, the sputum suction tube 4 is first used for performing sputum suction of the lungs and respiratory tract via the endotracheal tube 10. In the subsequent stage of sucking expectoration in the oral cavity 5, without detaching the retaining seat 3 from the main body 1, by changing the relative position of the retaining seat 3 and the main body 1, the sputum suction tube 4 is inserted in the oral cavity 5 smoothly via the open portion 12 to suck the expectoration in the oral cavity 5 for the patient. The operation is very convenient. In addition to sputum suction, by changing the relative position between the retaining seat 3 and the main body 1, a toothbrush may be inserted in the patient's mouth via the open portion 12 to brush the patient's teeth, without detaching the retaining seat 3 from the main body 1, or other nursing utensils are used to stretch into the oral cavity 5 for performing relevant nursing care.

Figure 7:
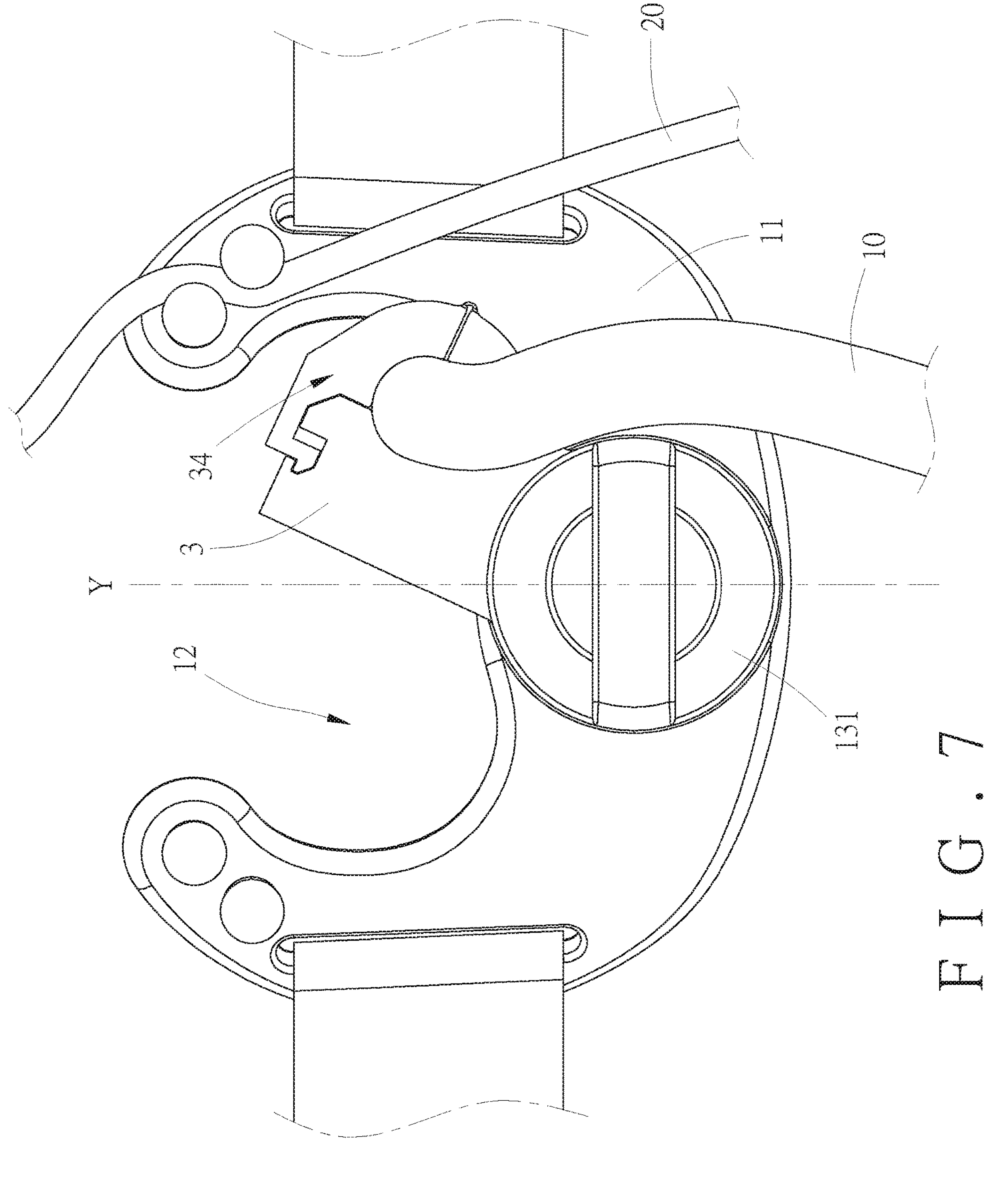
FIG. 7 is a third schematic view of the first embodiment used for performing sputum suction.

Referring to FIG. 1 and FIG. 7, when the movable cap 131 is unscrewed away from the protruding shaft 132 to be in the unlocking position, the retaining seat 3 is detached from the protruding shaft 132 and reversed to be installed on the solid portion 11. After that, the movable cap 131 is screwed to the protruding shaft 132 again. The first tube retaining portion 34 is located at the right side of the longitudinal centerline Y, and then the retaining seat 3 is rotated to the right. This is one of the operation modes of the present invention. By changing the relative position between the first tube retaining portion 34 and the open portion 12, in addition to nursing care such as sputum suction and brushing teeth, it is possible to prevent the endotracheal tube 10 from being retained at the same position of the oral cavity (not shown in FIG. 7) to cause ulceration of the oral cavity.

Figure 10:
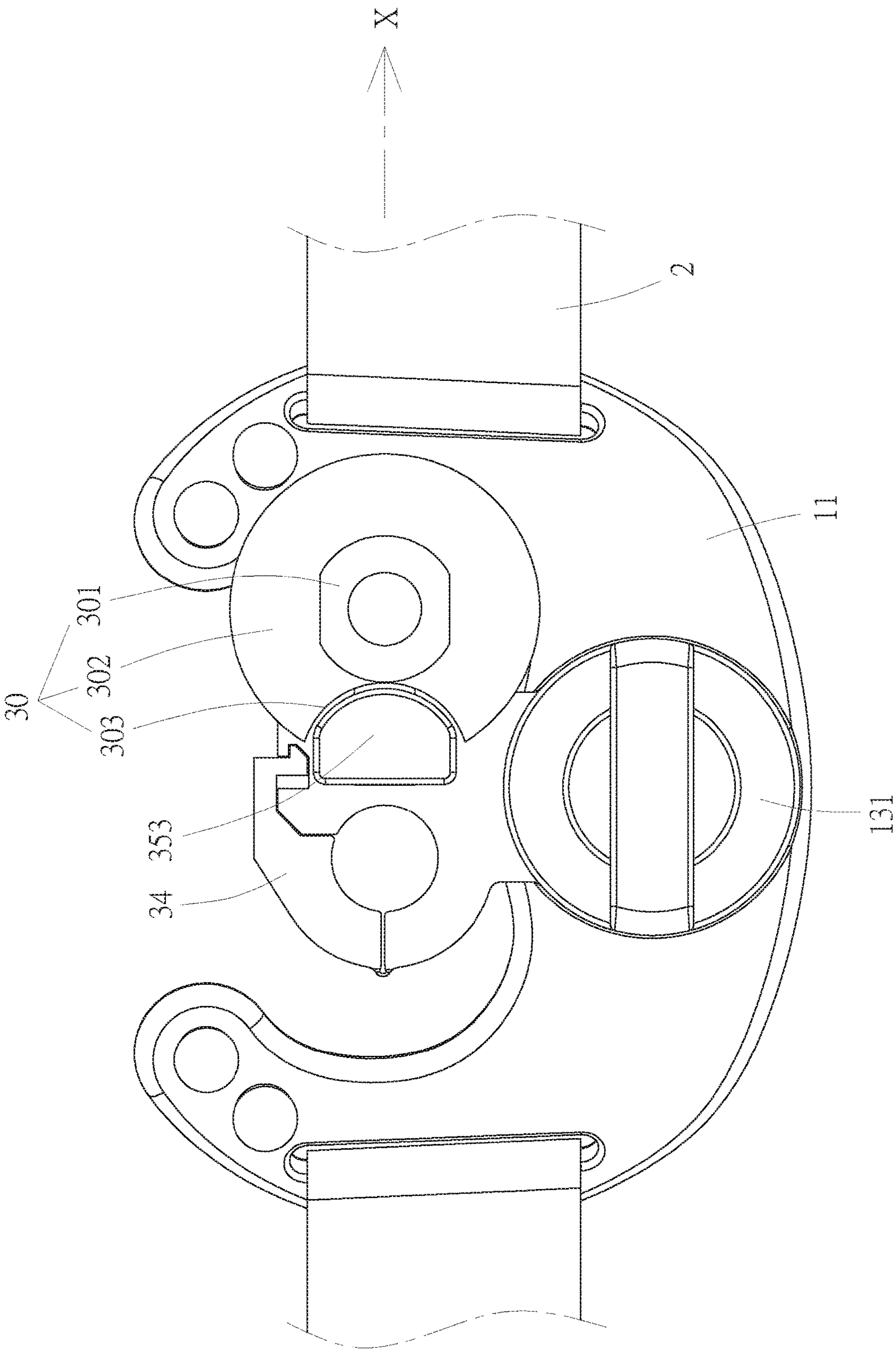
FIG. 10 is a first schematic view of the second embodiment used for mounting the bite block.
Figure 10A:
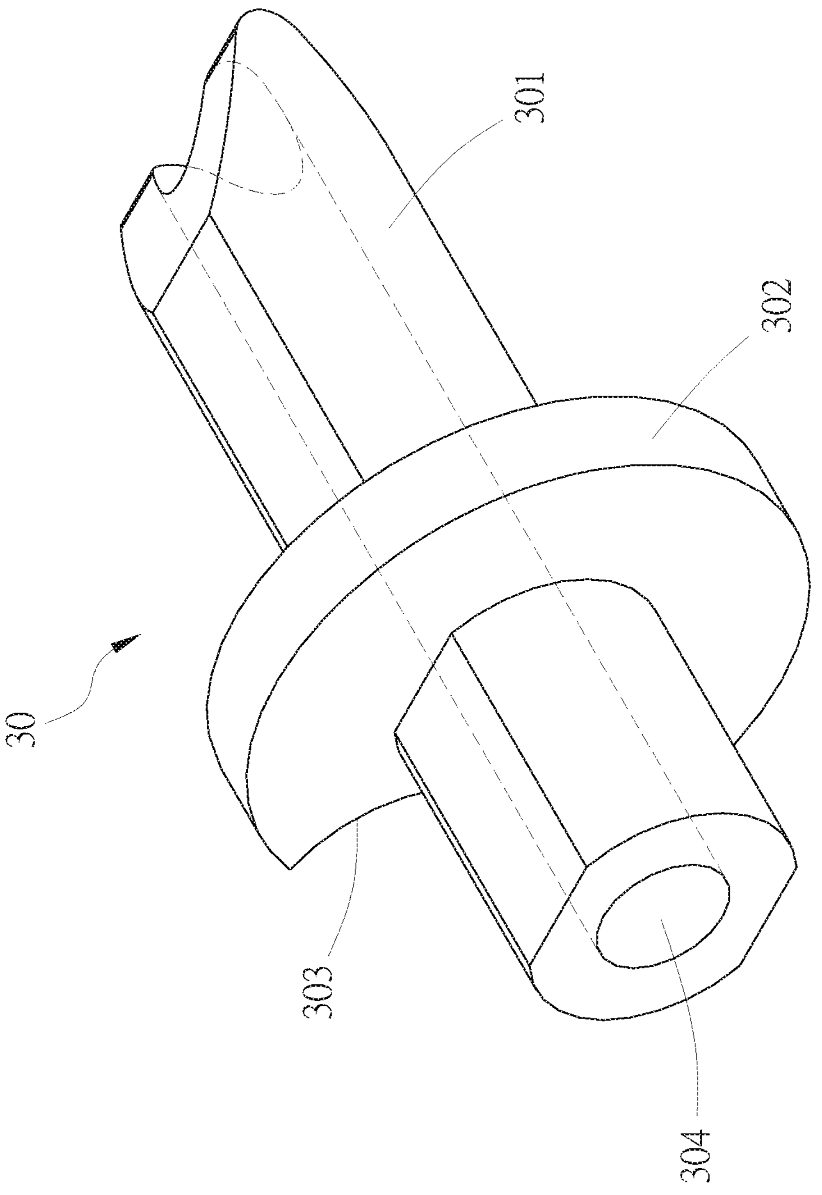
FIG. 10A is a perspective view of the bite block.

FIG. 8, FIG. 9, FIG. 10 and FIG. 10A illustrate a second embodiment of the retaining device for medical equipment of the present invention. The second embodiment is substantially similar to the first embodiment, except that the retaining seat 3 further includes a bite block holder 35. The bite block holder 35 is configured to hold a bite block 30. The bite block 30 includes a bite portion 301, a holding portion 302, and a through hole 304 extending axially. The holding portion 302 is a block having an appropriate thickness and surrounds the periphery of the bite portion 301. A notch 303 is formed on the holding portion 302. The bite block 30 is configured to prevent the patient from biting the endotracheal tube 10 to affect the circulation of gas. FIG. 10A shows the structure of the bite block 30.

The first tube retaining portion 34 and the bite block holder 35 are arranged along a transverse direction X in a straight line or a curved line. In this embodiment, the first tube retaining portion 34 and the bite block holder 35 are arranged in a straight line. When the patient uses the bite block 30, the bite block holder 35 corresponds in position to the open portion 12. When the retaining seat 3 is detached and reversed or rotated, the relative position between the first tube retaining portion 34/the bite block holder 35 and the open portion 12 is also changed.

The bite block holder 35 includes an opening 351 and a stopper 352. The stopper 352 includes a first clamp plate 353 and a second clamp plate 354. The first clamp plate 353 and the second clamp plate 354 are formed on two opposite ends of the stopper 352, respectively. Both the first clamp plate 353 and the second clamp plate 354 correspond in shape to the notch 303 of the bite block 30, and are in the form of a flat plate. The stopper 352 passes through and is movable on the retaining seat 3. The stopper 352 slides back and forth along the insertion direction Z in a manner of passing through the retaining seat, thereby selectively forming a first holding groove 353A (referring to FIG. 11A) between the first clamp plate 353 and the first face 31 or a second holding groove 354A between the second clamp plate 354 and the second face 32 (referring to FIG. 11B).

Referring to FIG. 8, FIG. 10, FIG. 10A, FIG. 11 and FIG. 11A, in this embodiment, the second face 32 of the retaining seat 3 is attached to the main body 1, and the first face 31 of the retaining seat 3 faces the movable cap 131. Therefore, the first holding groove 353 is formed between the first clamp plate 353 and the first face 31. When the bite block 30 is to be installed, the bite block 30 is pushed from the outside of the mouth toward the inside of the mouth, and the notch 303 of the bite block 30 is aligned with the first clamp plate 353. The holding portion 302 of the bite block 30 is rotated to be in the first holding groove 353A and the notch 303 is not aligned with the first clamp plate 353. That is to say, the bite block 30 can be inserted and positioned from the outside of the mouth to the inside of the mouth, without detaching the retaining seat 3 from the main body 1. When the bite block 30 is to be detached from the retaining seat 3, the bite block 30 is rotated for the notch 303 to be aligned with the first clamp plate 353, so that the bite block 30 is removed directly in a direction opposite to the insertion direction Z. With the structure of the bite block holder 35, it is very convenient to install and remove the bite block 30. In addition, the first clamp plate 353 and the second clamp plate 354 are in the form of a flat plate, which is less likely to scratch the lips of the human body.

Figure 8:
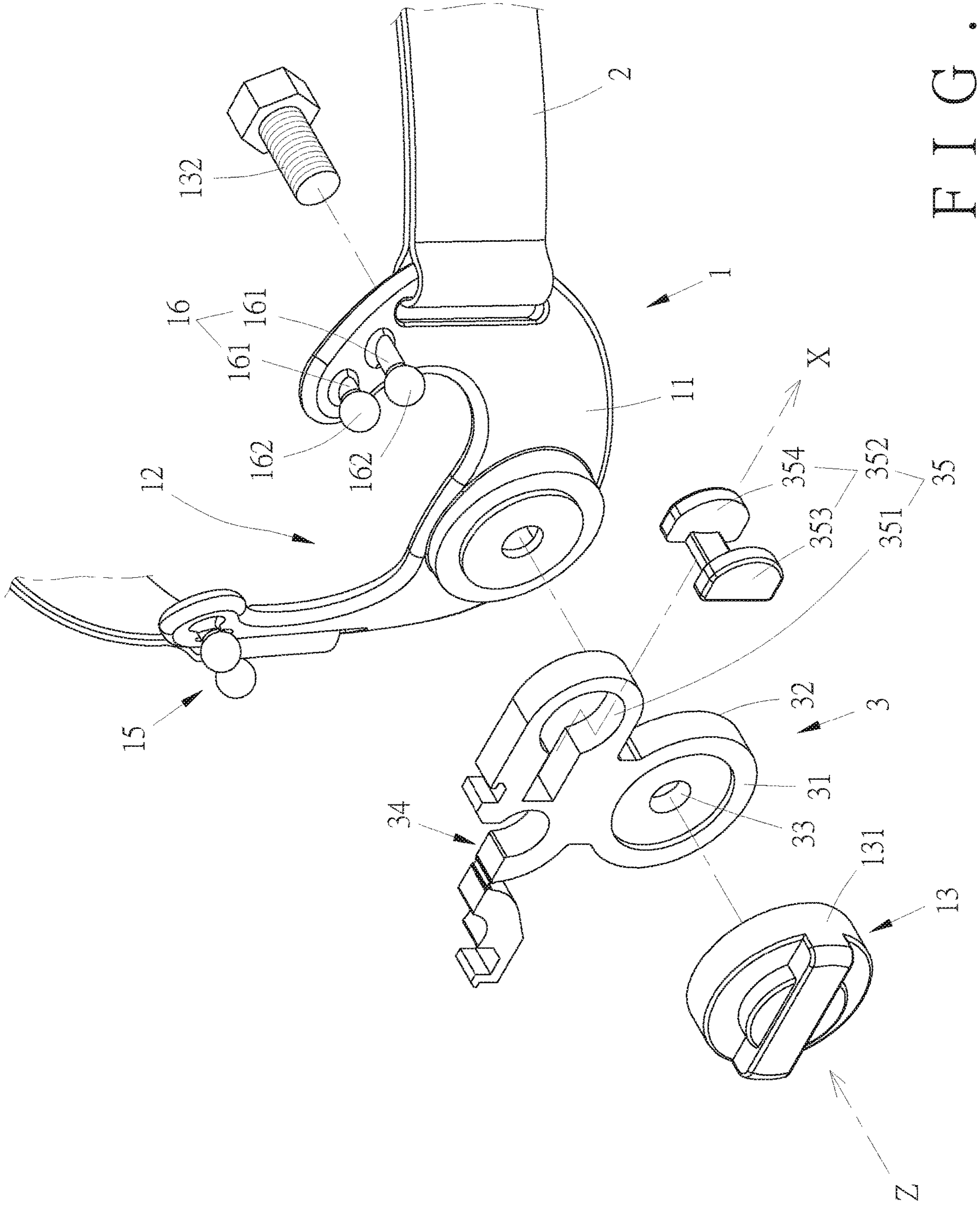
FIG. 8 is an exploded view of the retaining device for medical equipment according to a second embodiment of the present invention.
Figure 9:
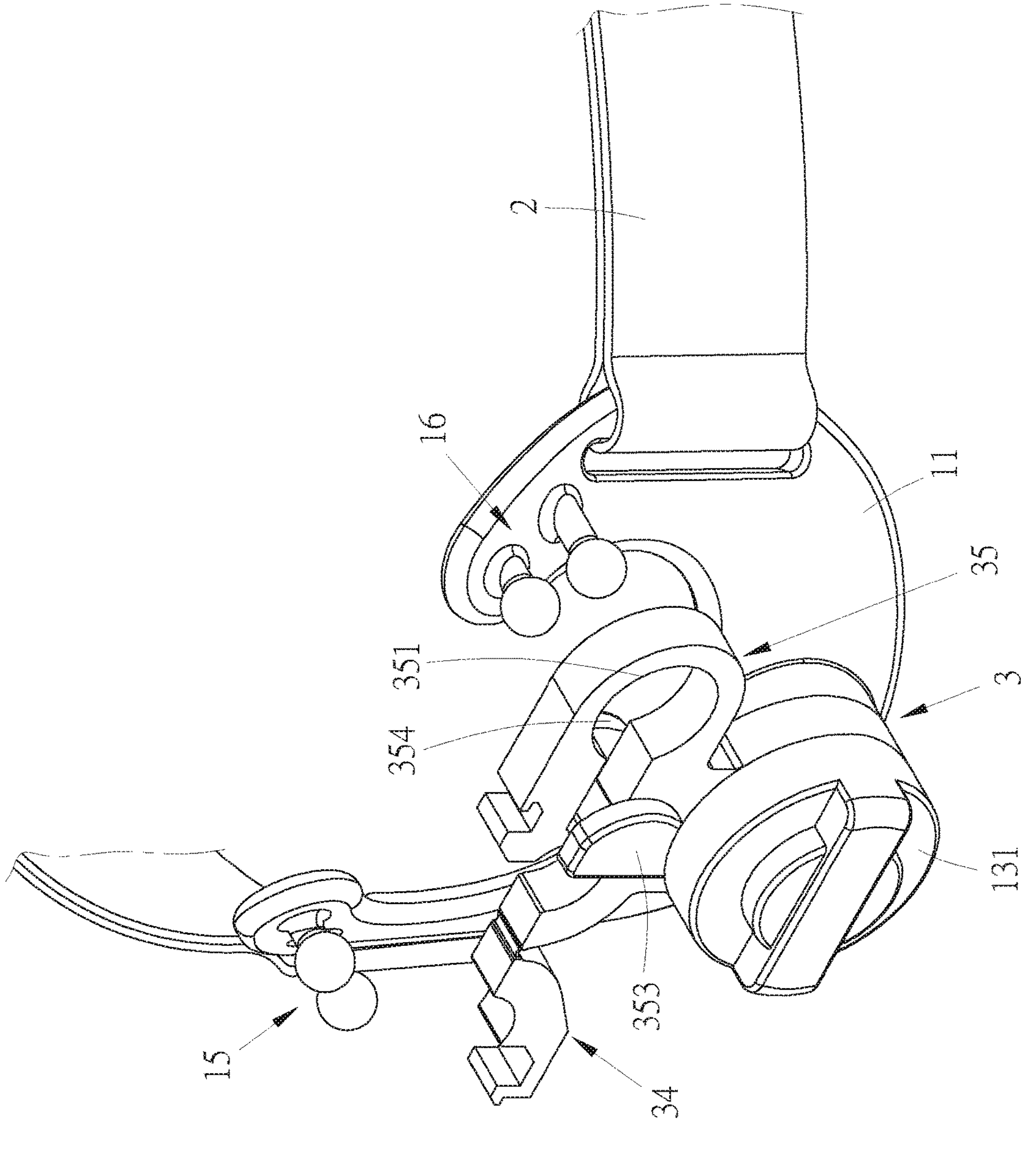
FIG. 9 is a perspective view of the second embodiment.
Figure 11:
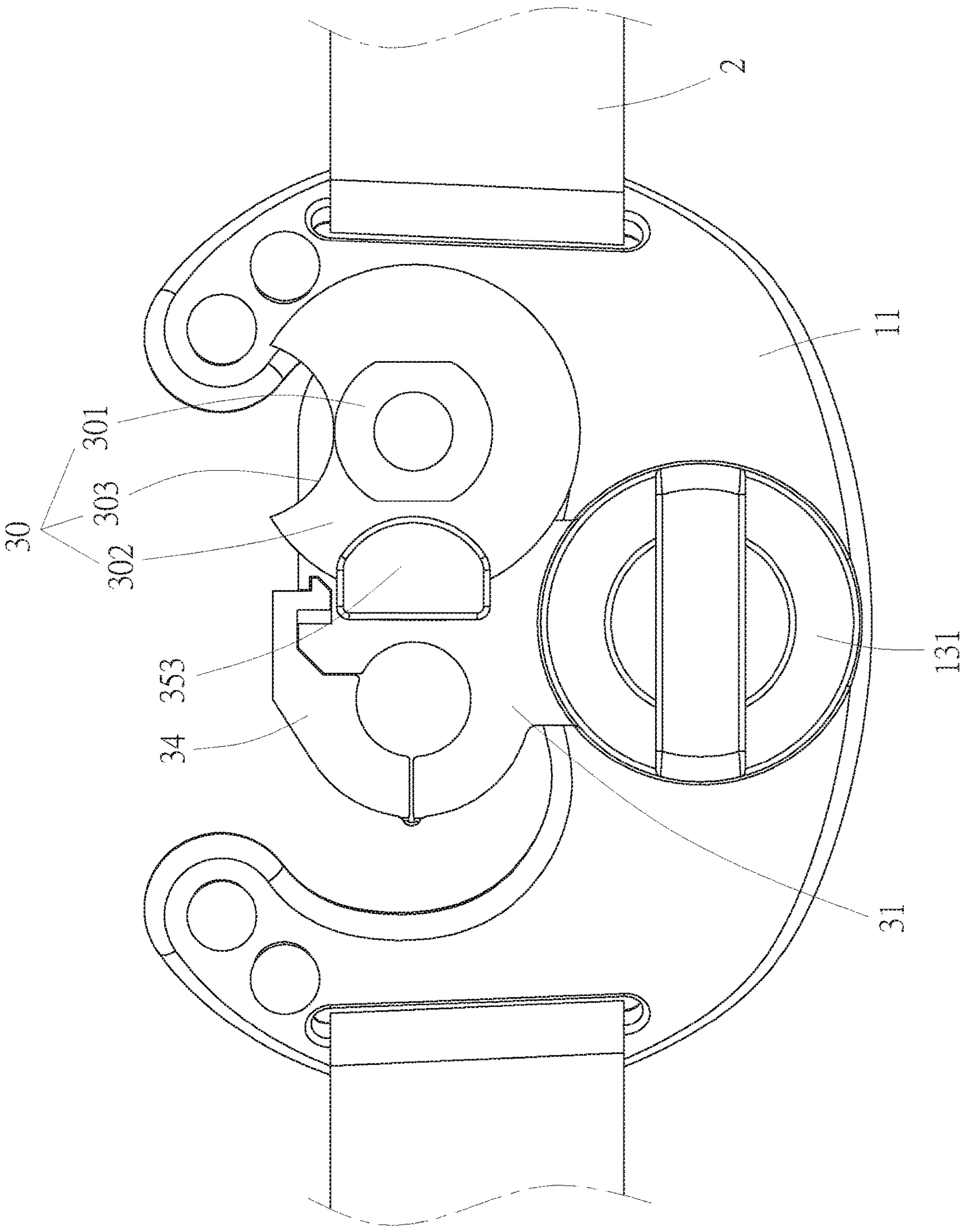
FIG. 11 is a second schematic view of the second embodiment used for mounting the bite block.
Figure 11A:
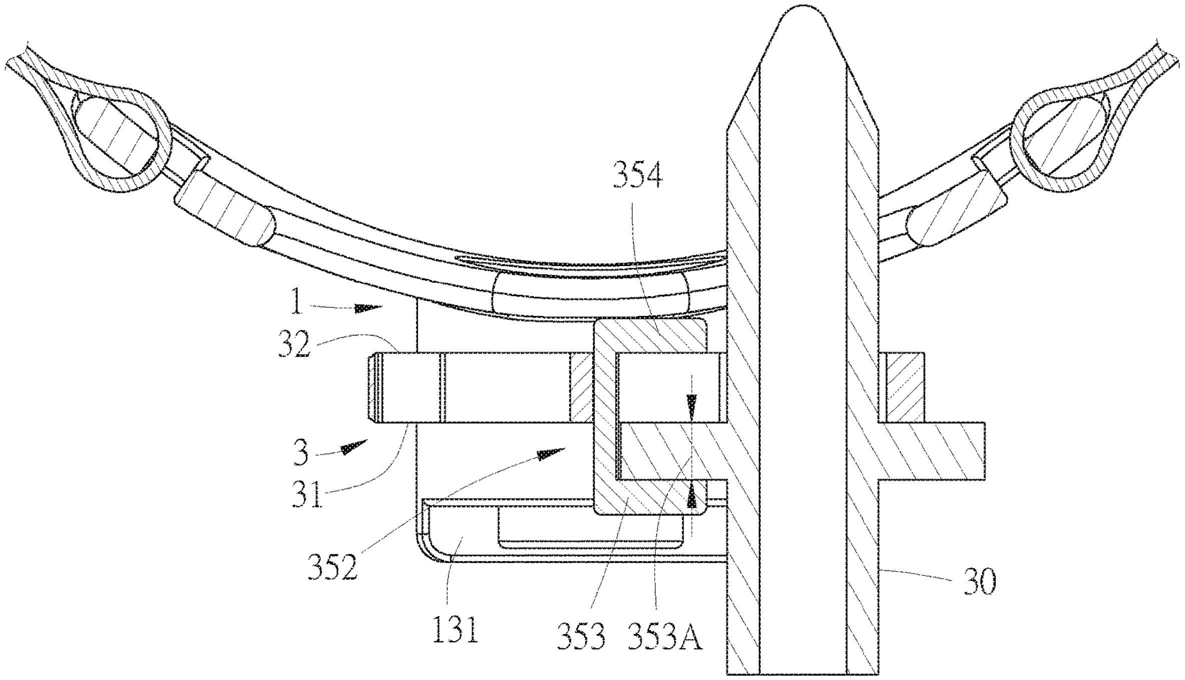
FIG. 11A is a sectional schematic view of the second embodiment mounted with the bite block.
Figure 11B:
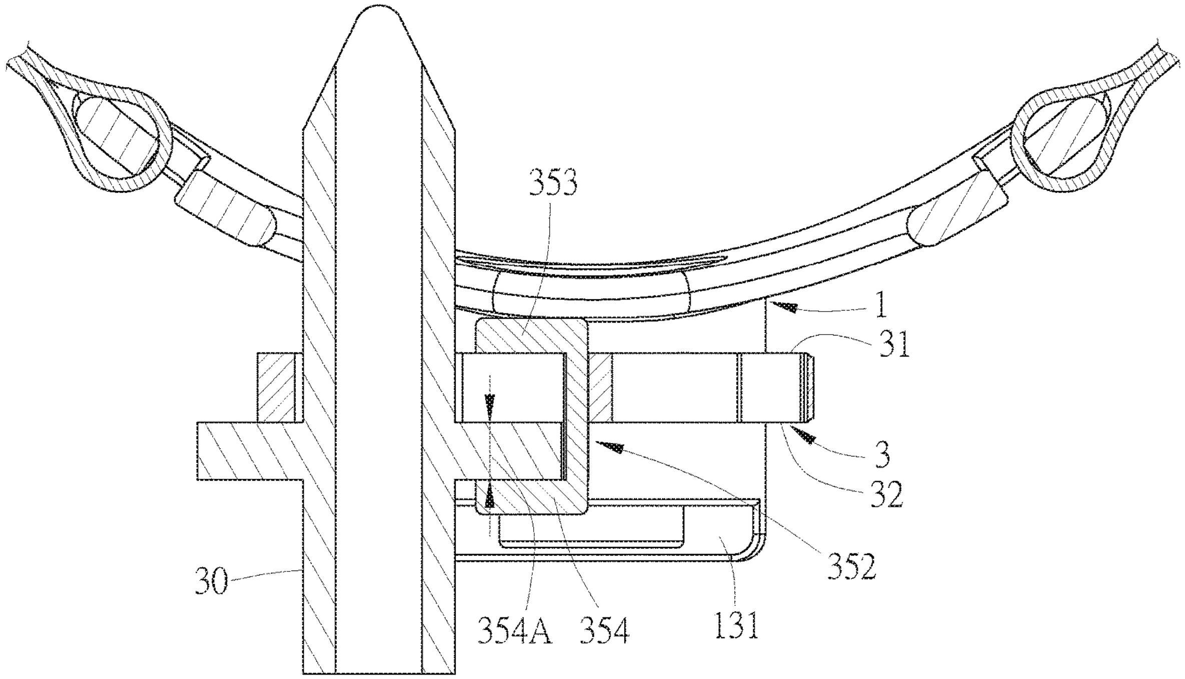
FIG. 11B is another sectional schematic view of the second embodiment mounted with the bite block, wherein the retaining seat is reversed.

Please refer to FIG. 8, FIG. 10A and FIG. 11 B. When the retaining seat 3 is detached and reversed for the first face 31 to be attached to the main body 1, the stopper 352 slides to form the second holding groove 354A between the second clamp plate 354 and the second face 32. When the bite block 30 is to be installed, the notch 303 of the bite block 30 is aligned with the second clamp plate 354. The holding portion 302 of the bite block 30 is rotated to be in the second holding groove 354A and the notch 303 is not aligned with the second clamp plate 354, such that the bite block 30 is positioned. When the bite block 30 is to be detached from the retaining seat 3, the bite block 30 is rotated for the notch 303 to be aligned with the second clamp plate 354, so that the bite block 30 is removed in a direction opposite to the insertion direction Z.

Figure 12:
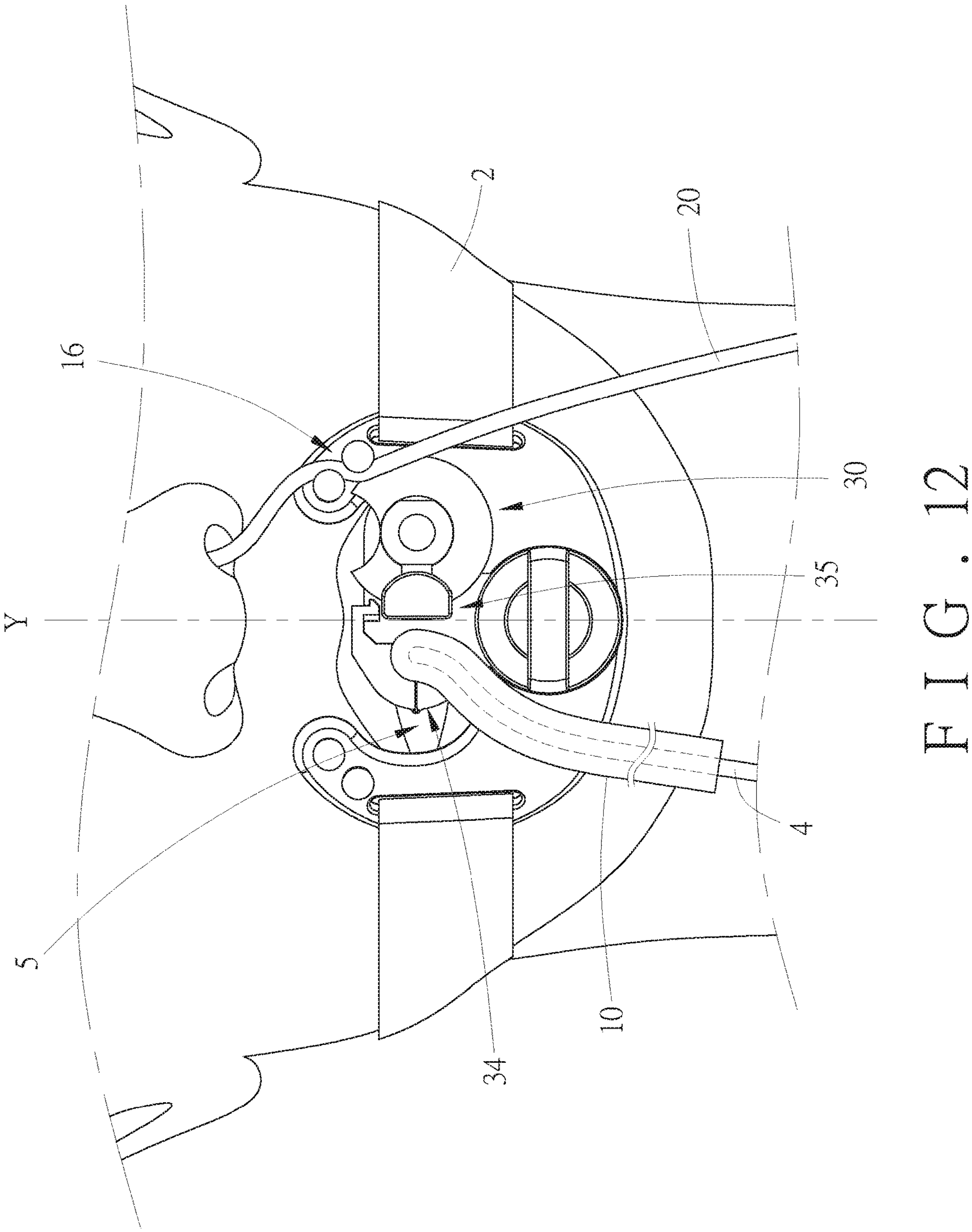
FIG. 12 is a first schematic view of the second embodiment used to retain the endotracheal tube, the nasogastric tube and the bite block for performing sputum suction.

Referring to FIG. 12, when it is necessary to retain medical equipment, such as the endotracheal tube 10, the nasogastric tube 20, the orogastric tube or the bite block 30, similar to the first embodiment, the retaining device for medical equipment corresponds to the mouth of the human body, and the strap 2 is sleeved on the head of the human body. The endotracheal tube 10 is retained by the first tube retaining portion 34, and the nasogastric tube 20 is selectively retained by the main body second tube retaining portion 16. In this example, the bite block 30 is held by the bite block holder 35.

Figure 13:
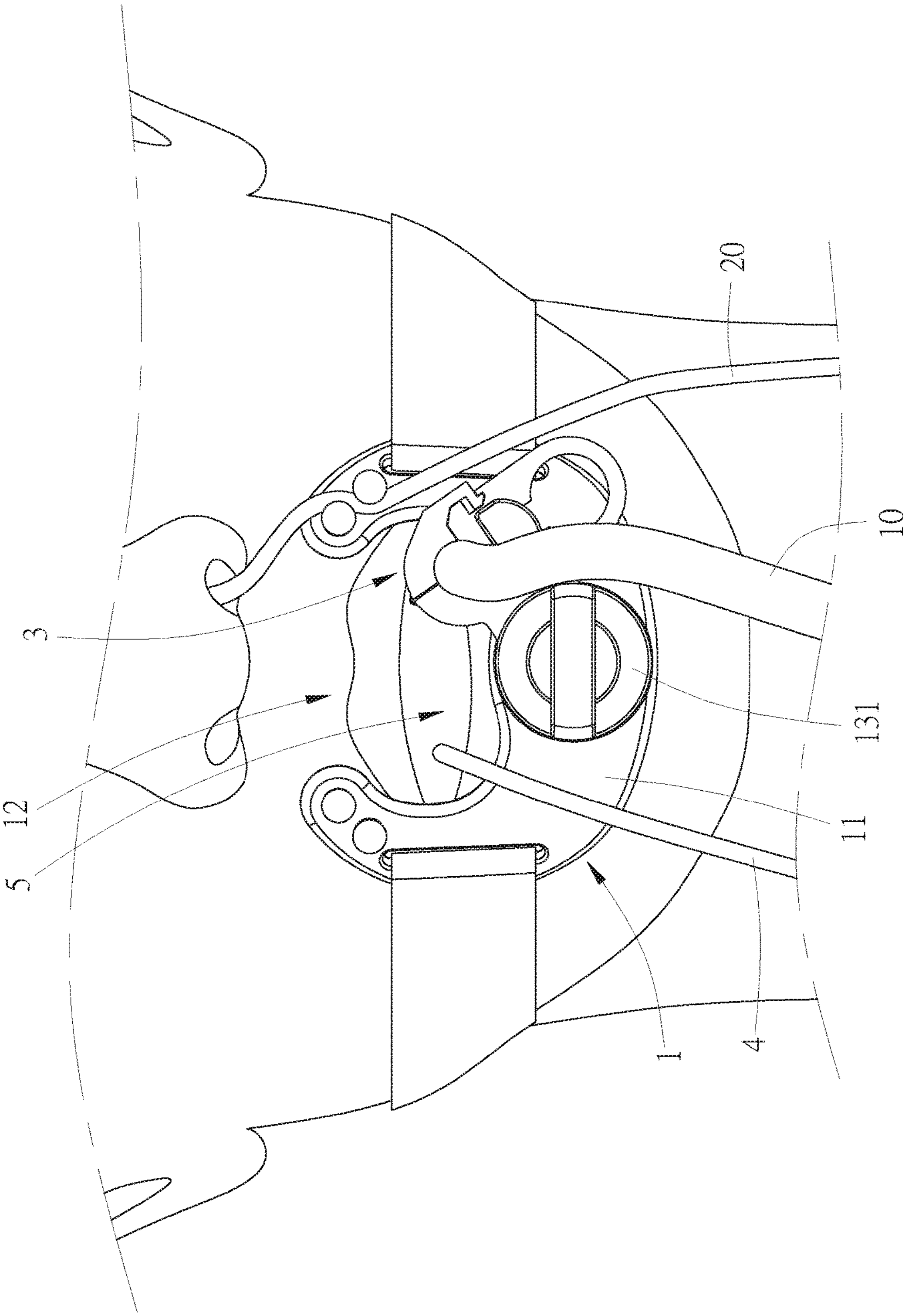
FIG. 13 is a second schematic view of the second embodiment used for performing sputum suction.
Figure 14:
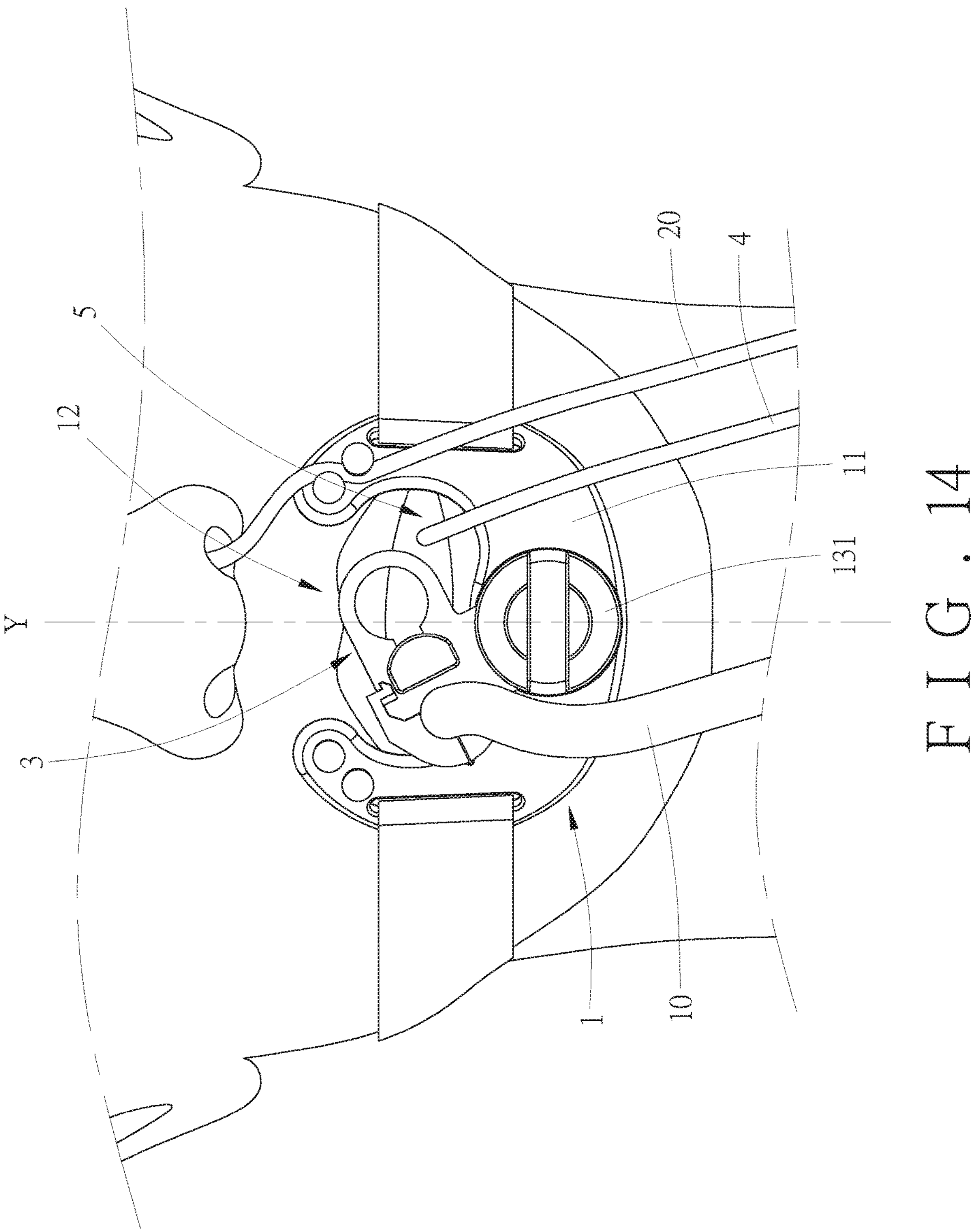
FIG. 14 is a third schematic view of the second embodiment used for performing sputum suction.
Figure 15:
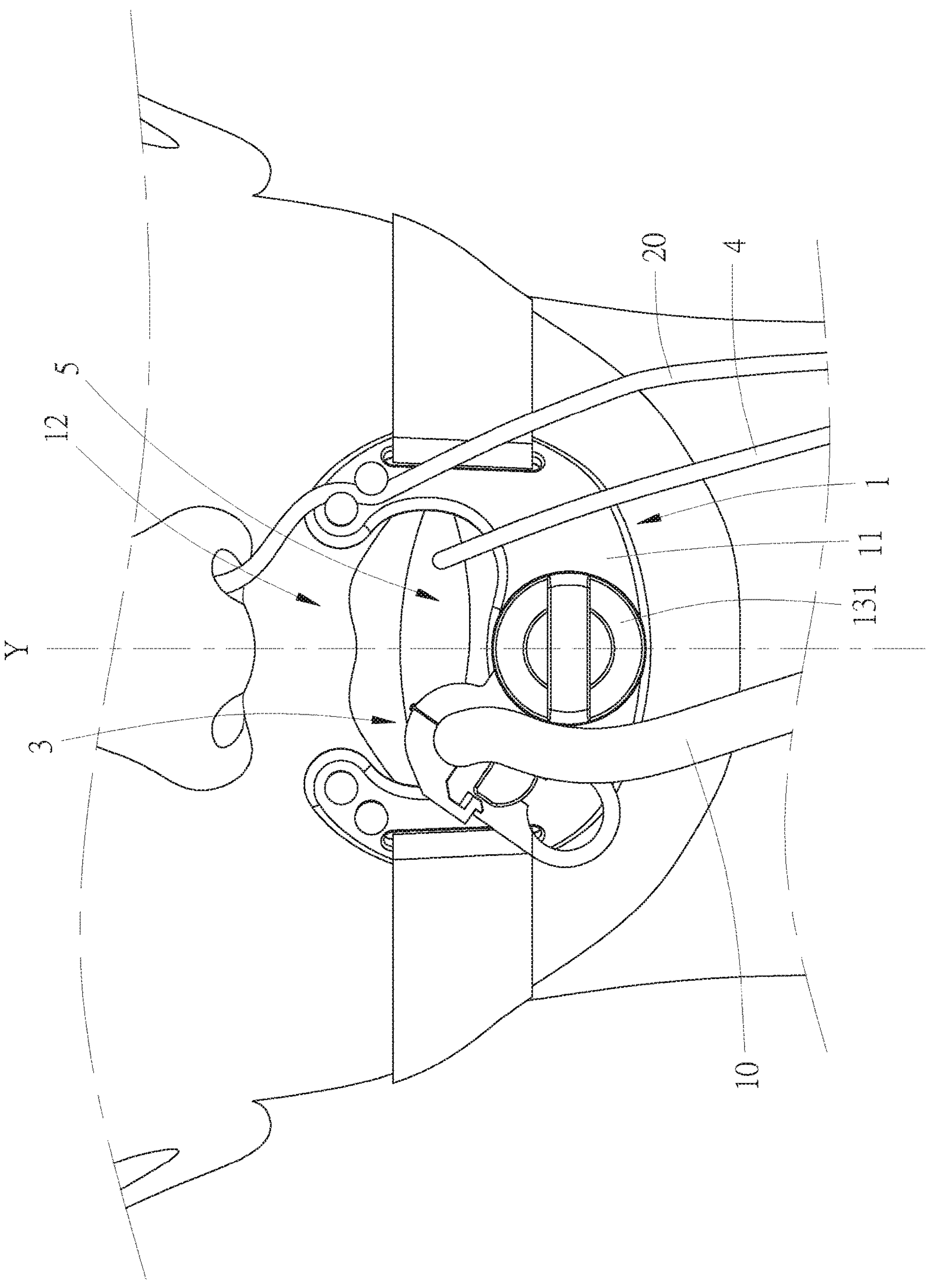
FIG. 15 is a fourth schematic view of the second embodiment used for performing sputum suction.
Figure 15A:
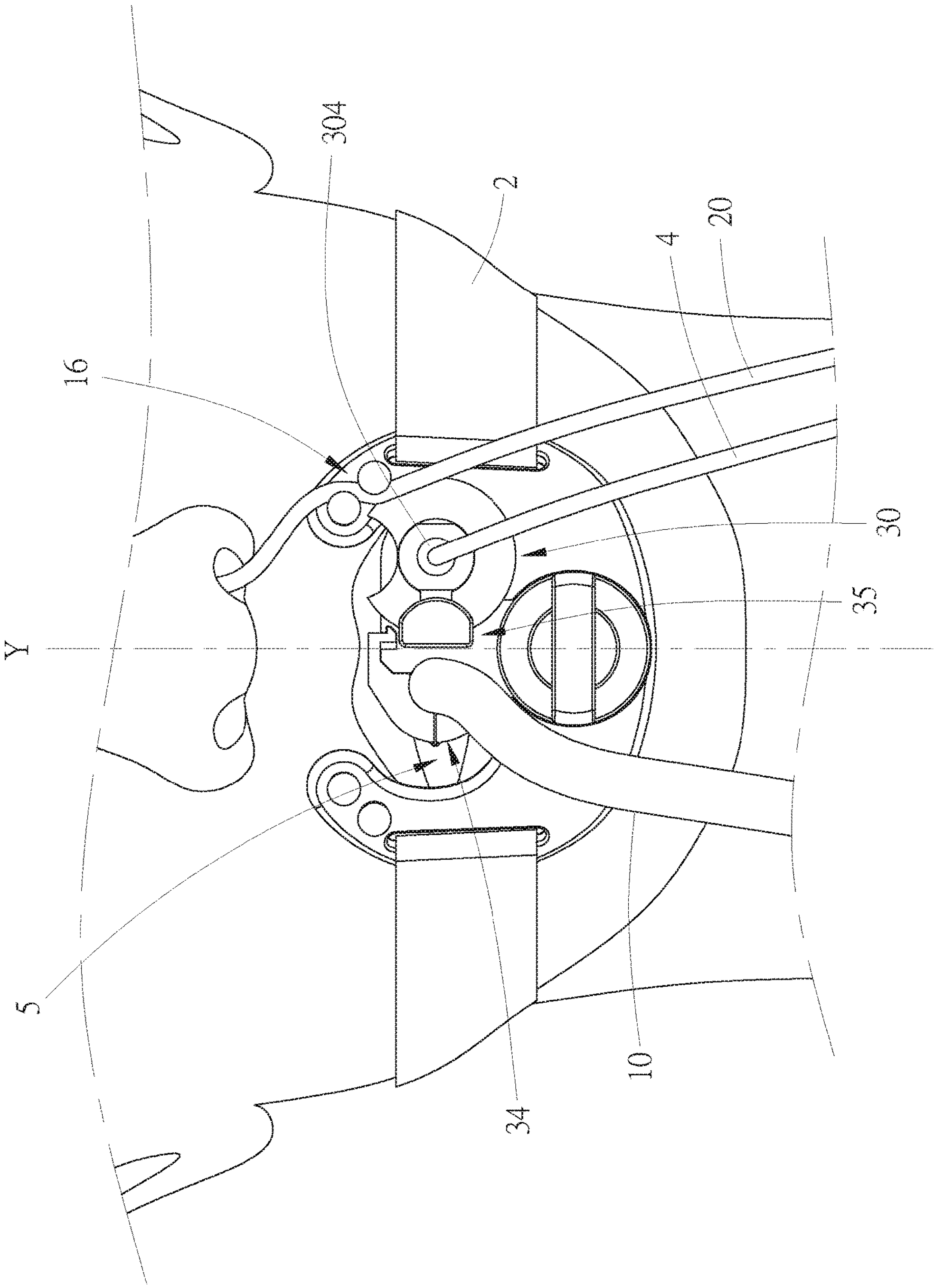
FIG. 15A is a schematic view of the second embodiment used for performing sputum suction via the sputum section tube passing through the bite block.

Referring to FIG. 12, after the sputum suction tube 4 is inserted through the endotracheal tube 10 to suck the sputum from the lungs and respiratory tract of the patient, the sputum suction tube 4 is inserted in the oral cavity 5 of the patient to suck the expectoration in the oral cavity 5. Please refer to FIG. 13 to FIG. 15. When the expectoration in the oral cavity 5 is to be sucked, the bite block 30 is first removed (referring to FIG. 12). At this moment, the nursing staff or caregiver looks at the patient to prevent the patient from biting the endotracheal tube 10. Next, similar to the first embodiment, the movable cap 131 is unscrewed to be in the unlocking position, and the retaining seat 3 is rotated to the right relative to the main body 1 (as shown in FIG. 13). Then, the movable cap 131 is screwed to be in the locking position, so that the retaining seat 3 is secured. The sputum suction tube 4 is inserted in the oral cavity 5 of the patient via the open portion 12, so as to suck the expectoration in the oral cavity 5 of the patient. As shown in FIG. 14, if the retaining seat 3 is rotated to the left relative to the main body 1, the sputum suction tube 4 is inserted in the oral cavity 5 of the patient via the open portion 12, so as to suck the expectoration in the oral cavity 5 of the patient. If a larger space of the open portion 12 is required, referring to FIG. 13, the movable cap 131 is screwed away from the protruding shaft 132 (referring to FIG. 8) to be in the unlocking position. The retaining seat 3 is detached and reversed and then mounted to the solid portion 11 again, and the retaining seat 3 is rotated to the left relative to the solid portion 11. Then, the movable cap 131 is screwed to be in the locking position, so that the retaining seat 3 is secured. Thus, a larger space of the open portion 12 can be obtained. The sputum suction tube 4 is inserted in the oral cavity 5 of the patient via the open portion 12, so as to suck the expectoration in the oral cavity 5 of the patient. The retaining seat 3 is movable relative to the main body 1, so that a toothbrush or other care implements may be inserted in the patient's mouth via the open portion 12 to brush the patient's teeth or perform other oral care for the patient. Please refer to FIG. 15A. In the above operation, if the bite block 30 is not removed, the sputum suction tube 4 may be inserted in the oral cavity 5 of the patient via the through hole 304 of the bite block 30 to suck the expectoration in the oral cavity 5.

In the embodiments shown in FIG. 8 to FIG. 15A, the retaining seat 3 may not have the first tube retaining portion 34. That is, the retaining seat 3 is only provided with the bite block holder 35, which is also a feasible implementation of the present invention. In this implementation, the present invention may be used for retaining the bite block 30. The operation is the same as the foregoing operation. The position of the retaining seat 3 to be changed is also the same as the foregoing operation.

The embodiments shown in FIG. 8 to FIG. 15A may be provided with the main body third tube retaining portion and the main body fourth tube retaining portion as shown in FIG. 4A for retaining the orogastric tube.

Figure 16:
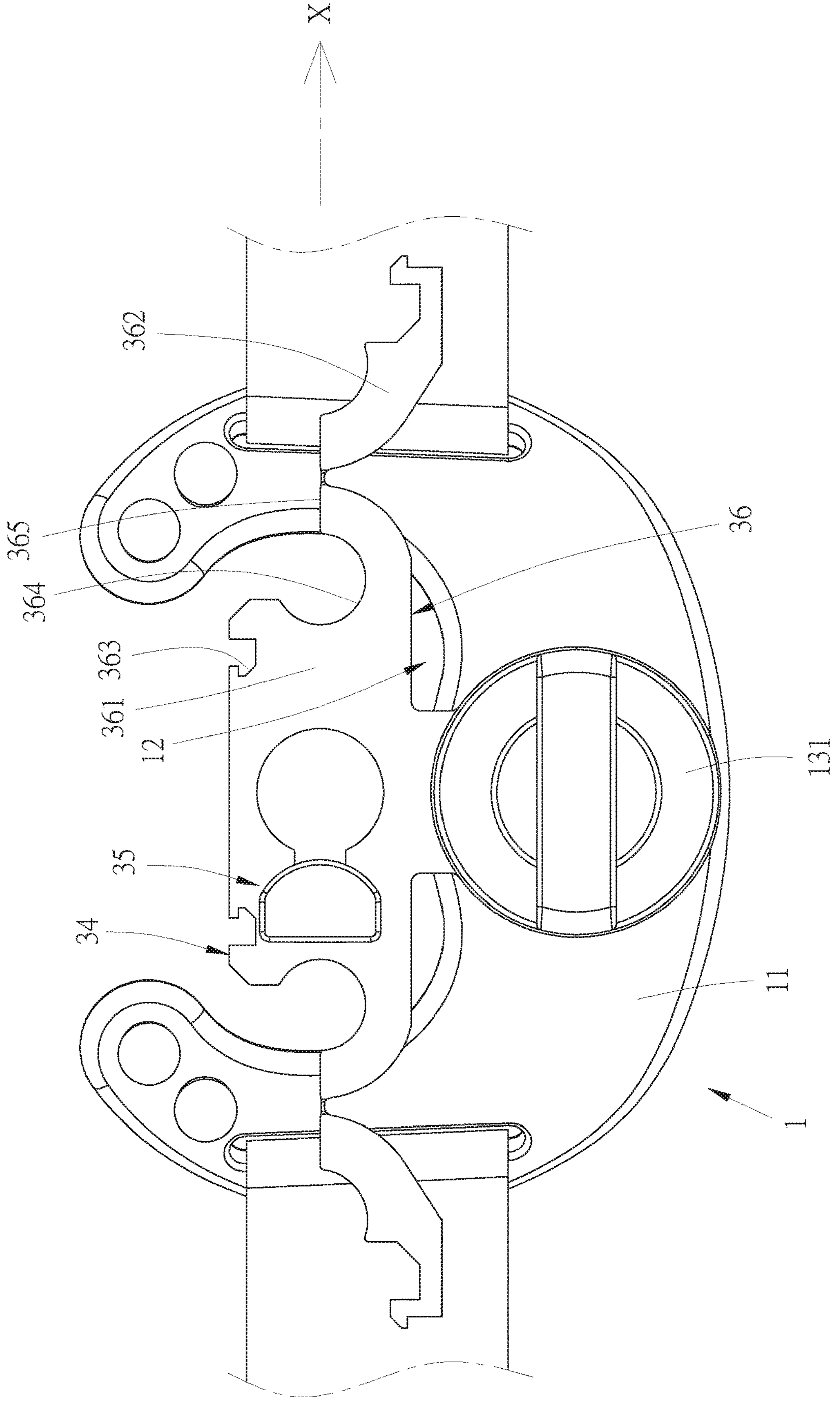
FIG. 16 is a planar view of the retaining device for medical equipment according to a third embodiment of the present invention.

FIG. 16 illustrates a third embodiment of the retaining device for medical equipment of the present invention. The third embodiment is substantially similar to the second embodiment, except that the retaining seat 3 further includes a second tube retaining portion 36.

The first tube retaining portion 34, the bite block holder 35 and the second tube retaining portion 36 are arranged along the transverse direction X. When the medical equipment, such as the endotracheal tube, needs to be retained by the second tube retaining portion 36, the second tube retaining portion 36 also corresponds in position to the open portion 12. When the retaining seat 3 is detached and reversed or rotated, the relative position between the first tube retaining portion 34/the bite block holder 35/the second tube retaining portion 36 and the open portion 12 is also changed.

The second tube retaining portion 36 is similar to the first tube retaining portion 34. The second tube retaining portion 36 includes a second base 361, a second fastener 362 and a second fastener groove 363. The second base 361 defines a second retaining hole 364 and forms a second positioning notch 365. The second retaining hole 364 communicates with the second positioning notch 365. The second fastener 362 is connected to the second base 361 via a thin film. The second fastener 362 is rotatable to be engaged in the second fastener groove 363 to close the second positioning notch 365, so that the second retaining hole 364 is in a completely closed state. Preferably, the material of the base 341 having the retaining hole 344 is an elastic material.

Figure 17:
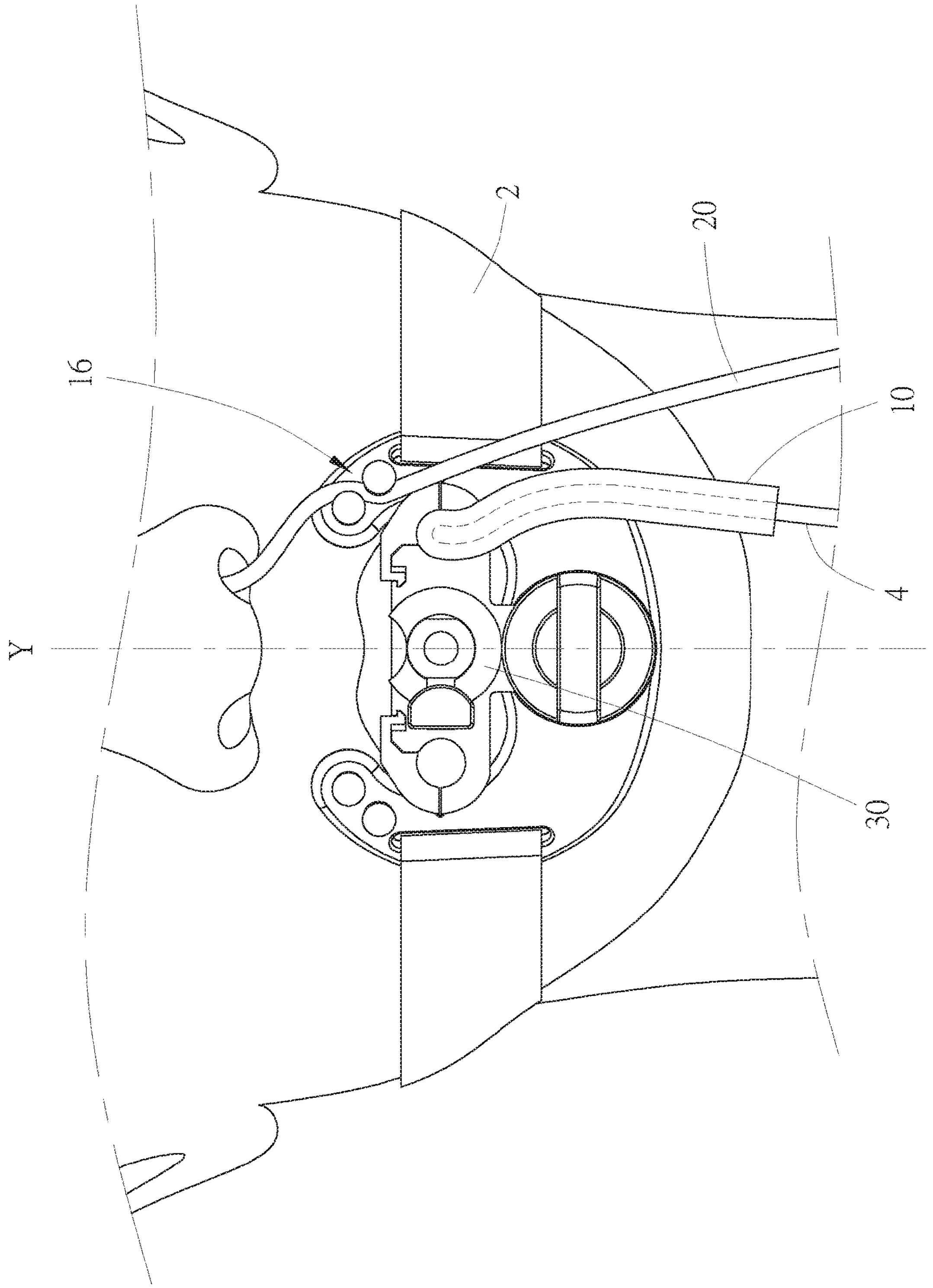
FIG. 17 is a first schematic view of the third embodiment used to retain the endotracheal tube, the nasogastric tube and the bite block for performing sputum suction.

Referring to FIG. 16 and FIG. 17, when it is necessary to retain medical equipment, such as the endotracheal tube 10, the nasogastric tube 20, the orogastric tube or the bite block 30, similar to the second embodiment, the strap 2 is sleeved on the human head so that the retaining device is secured on the human body. The endotracheal tube 10 is selectively retained by the first tube retaining portion 34 or the second tube retaining portion 36, the way to retain the endotracheal tube 10 is the same as the foregoing way, and will not be repeated here. The nasogastric tube 20 is selectively retained by the main body second tube retaining portion 16. The bite block 30 is held by the bite block holder 35.

Figure 18:
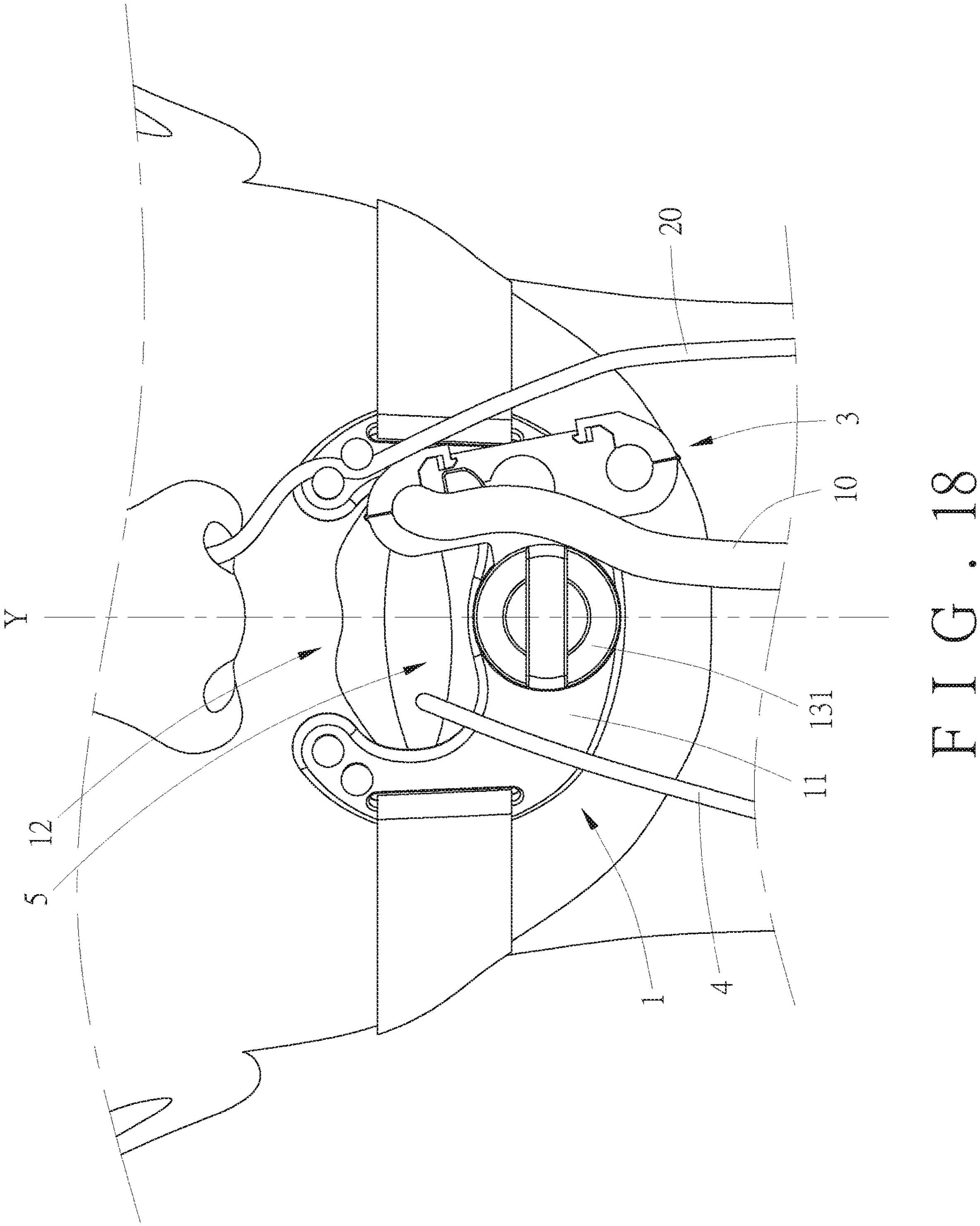
FIG. 18 is a second schematic view of the third embodiment used for performing sputum suction.
Figure 19:
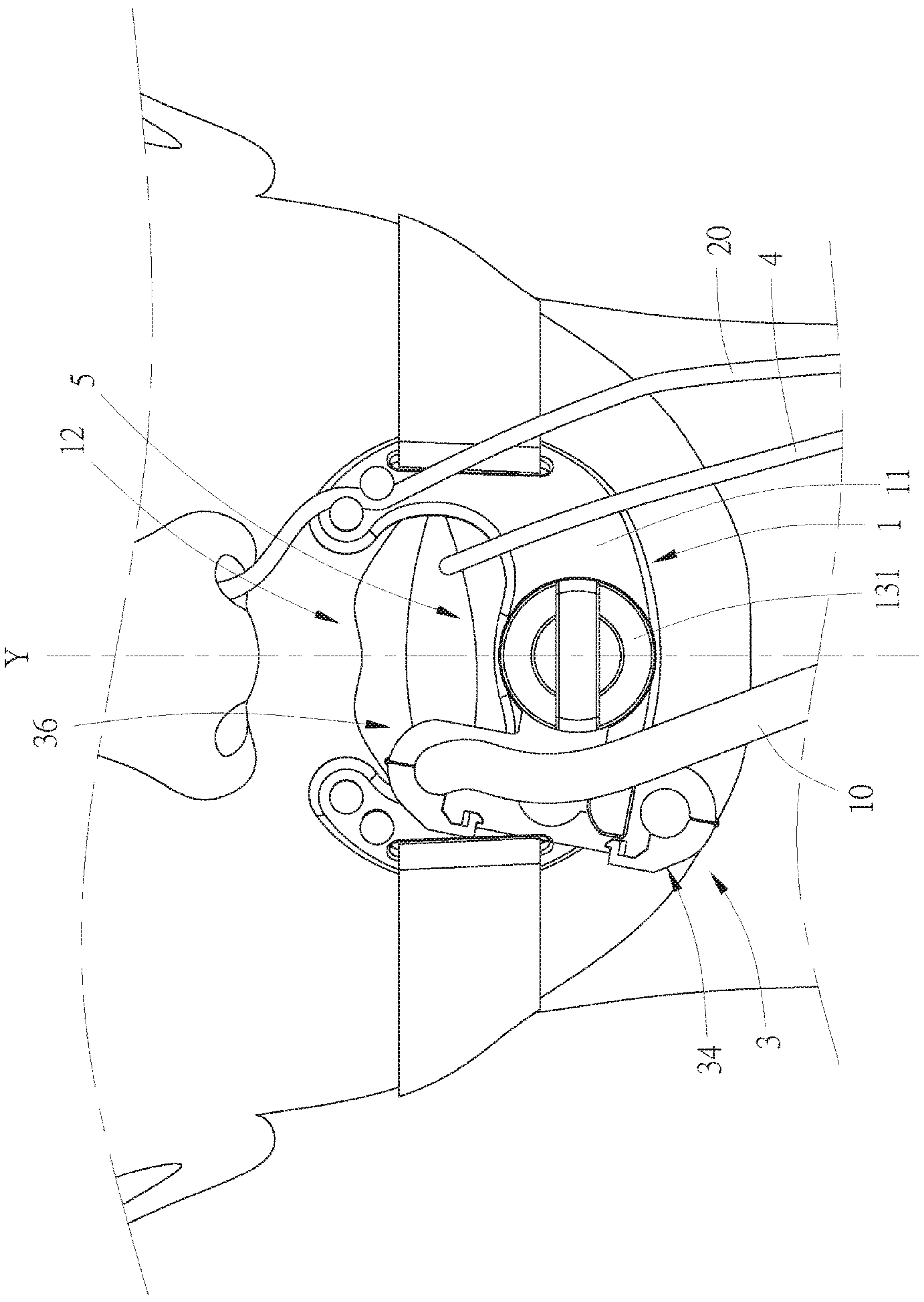
FIG. 19 is a third schematic view of the third embodiment used for performing sputum suction.
Figure 20:
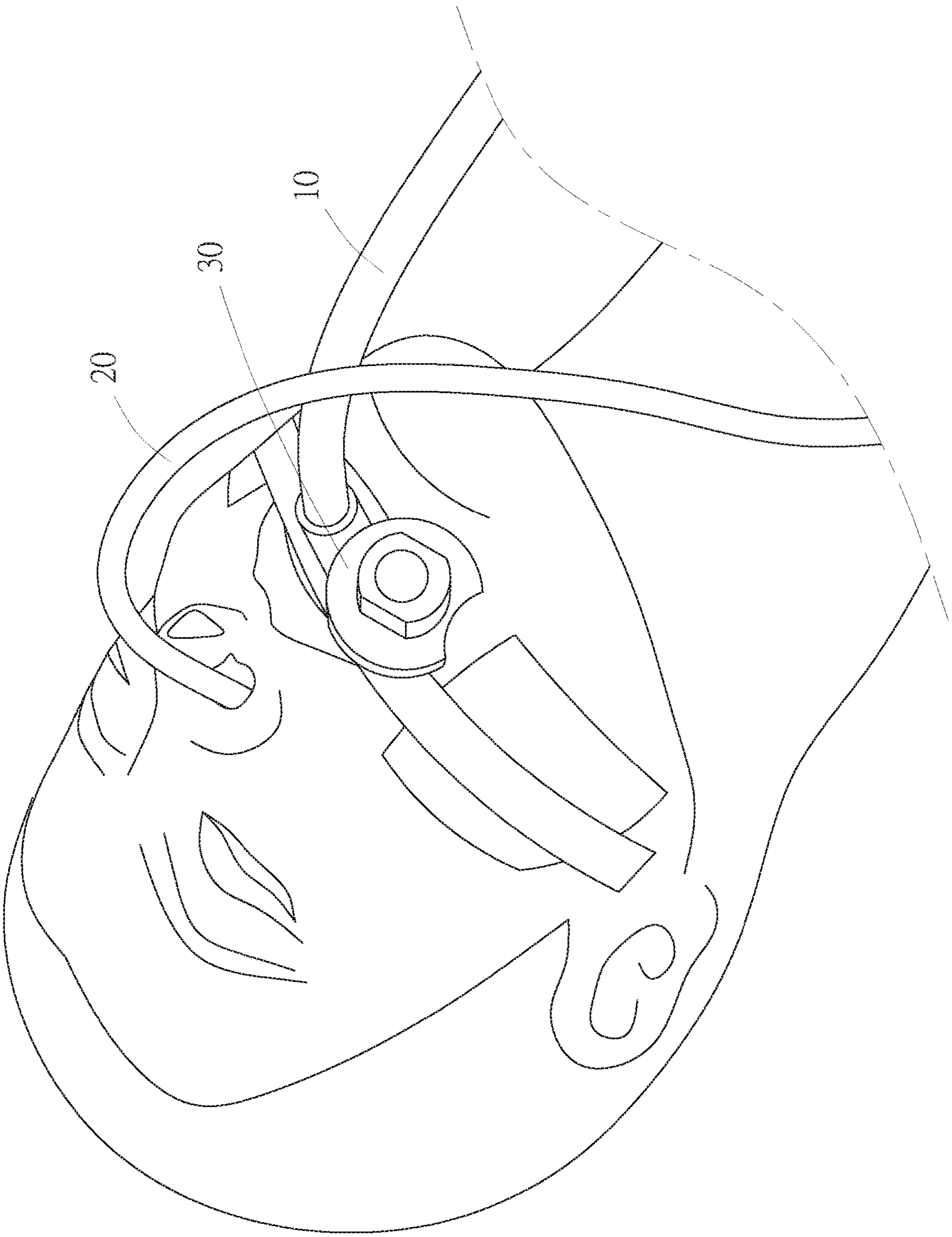
FIG. 20 a schematic view illustrating the traditional way to retain medical equipment.
Figure 21:
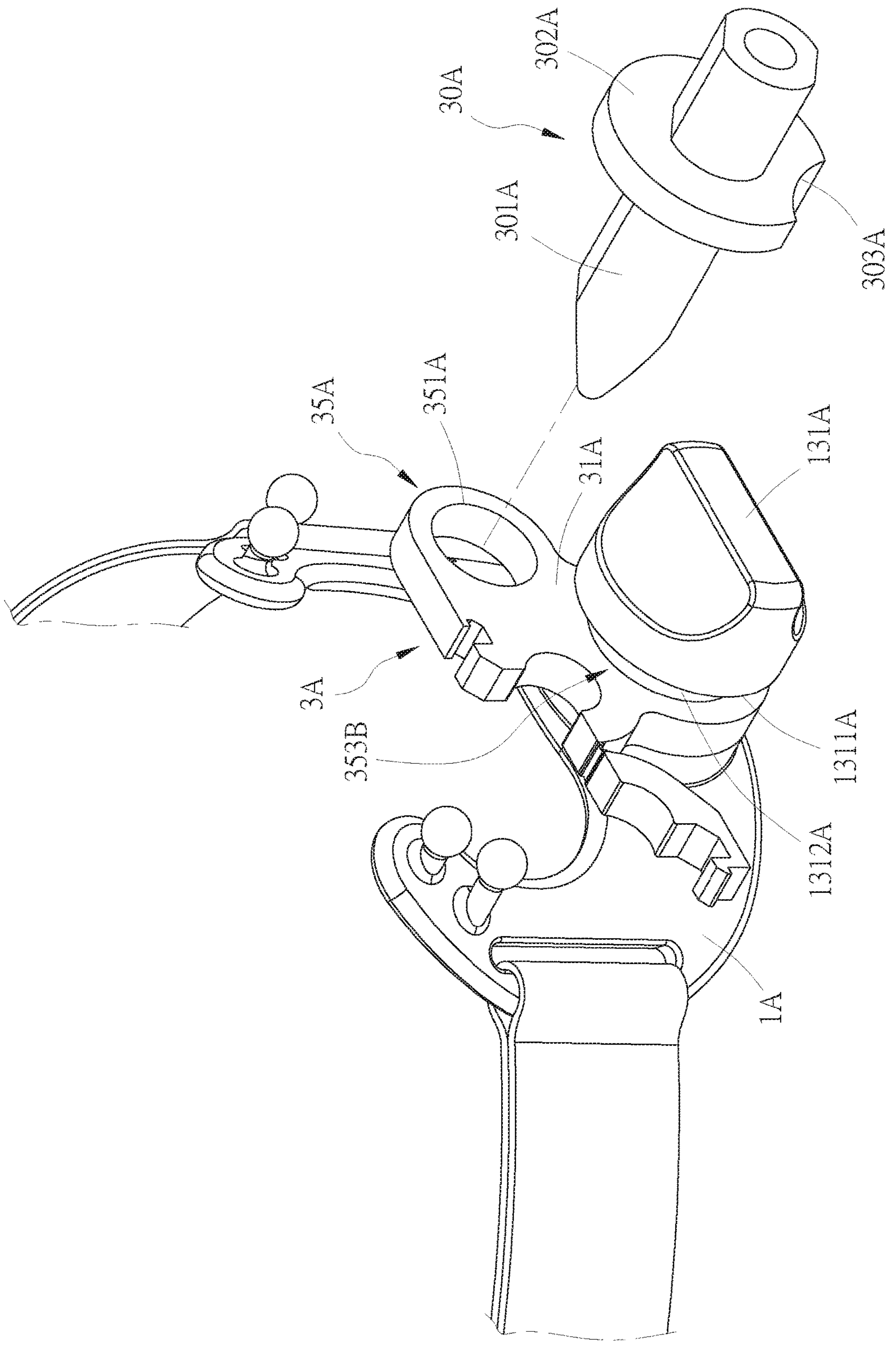
FIG. 21 is a perspective view according to a fourth embodiment of the present invention.
Figure 22:
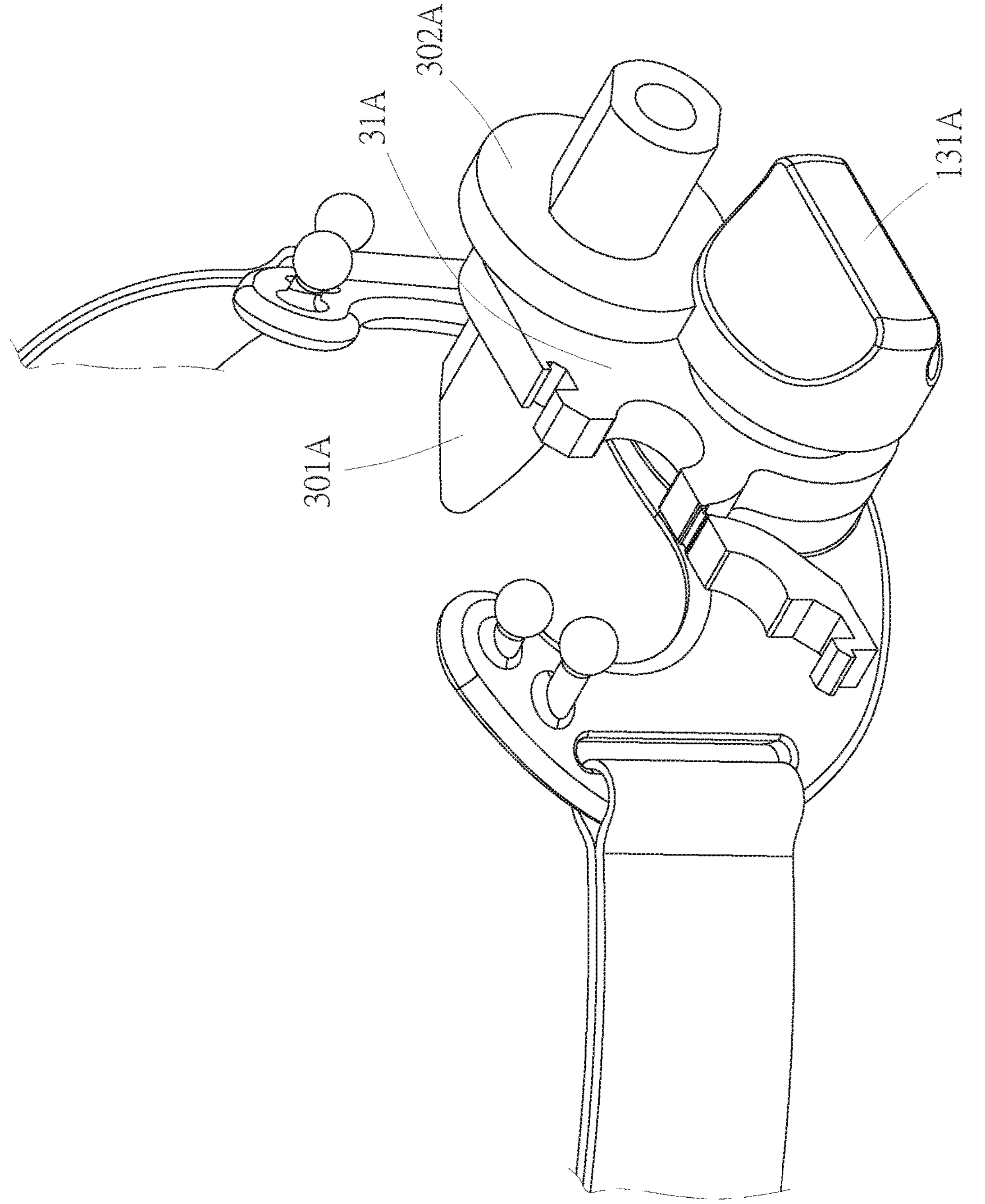
FIG. 22 is a first schematic view of the fourth embodiment mounted with the bite block.
Figure 23:
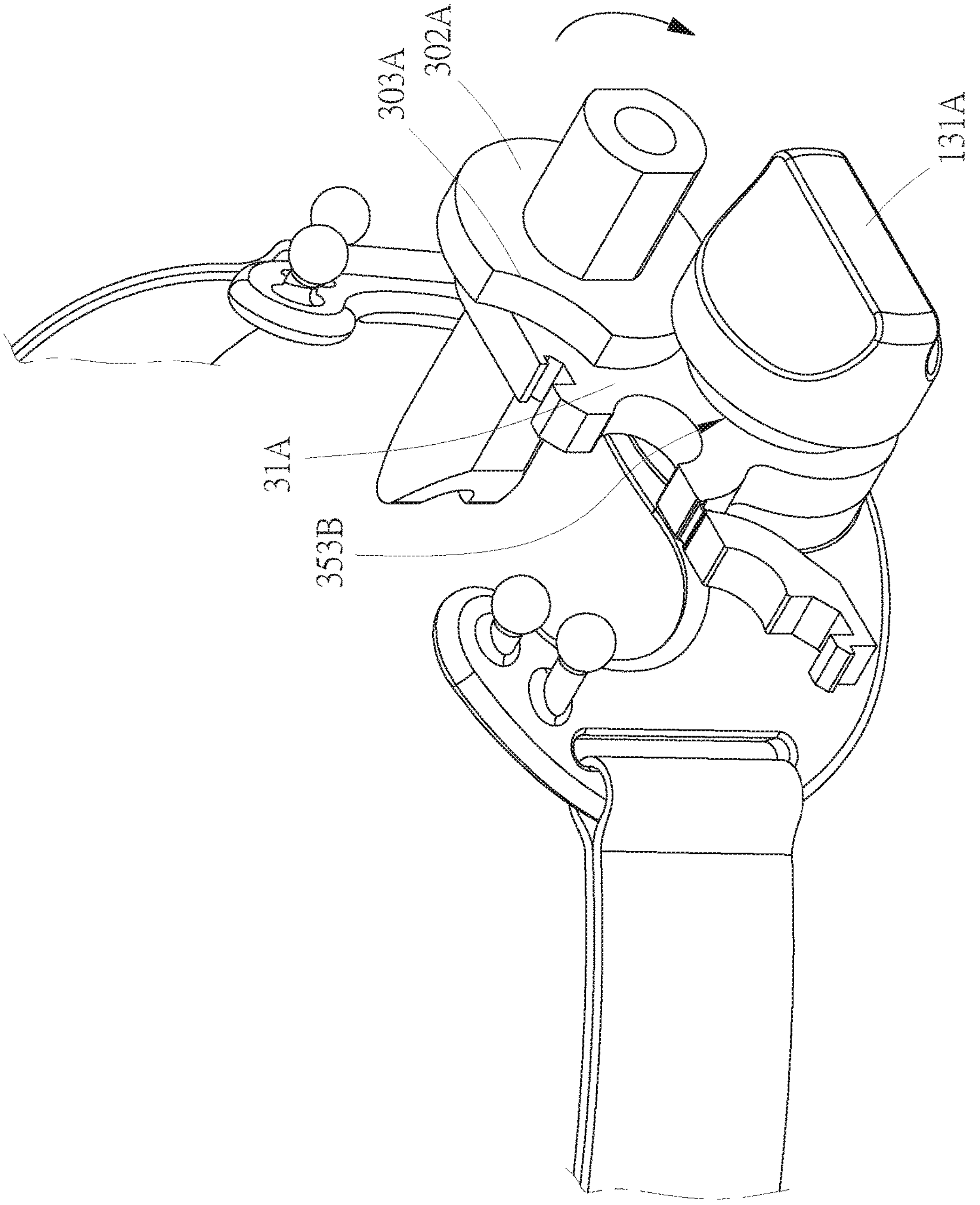
FIG. 23 is a second schematic view of the fourth embodiment mounted with the bite block.
Figure 24:
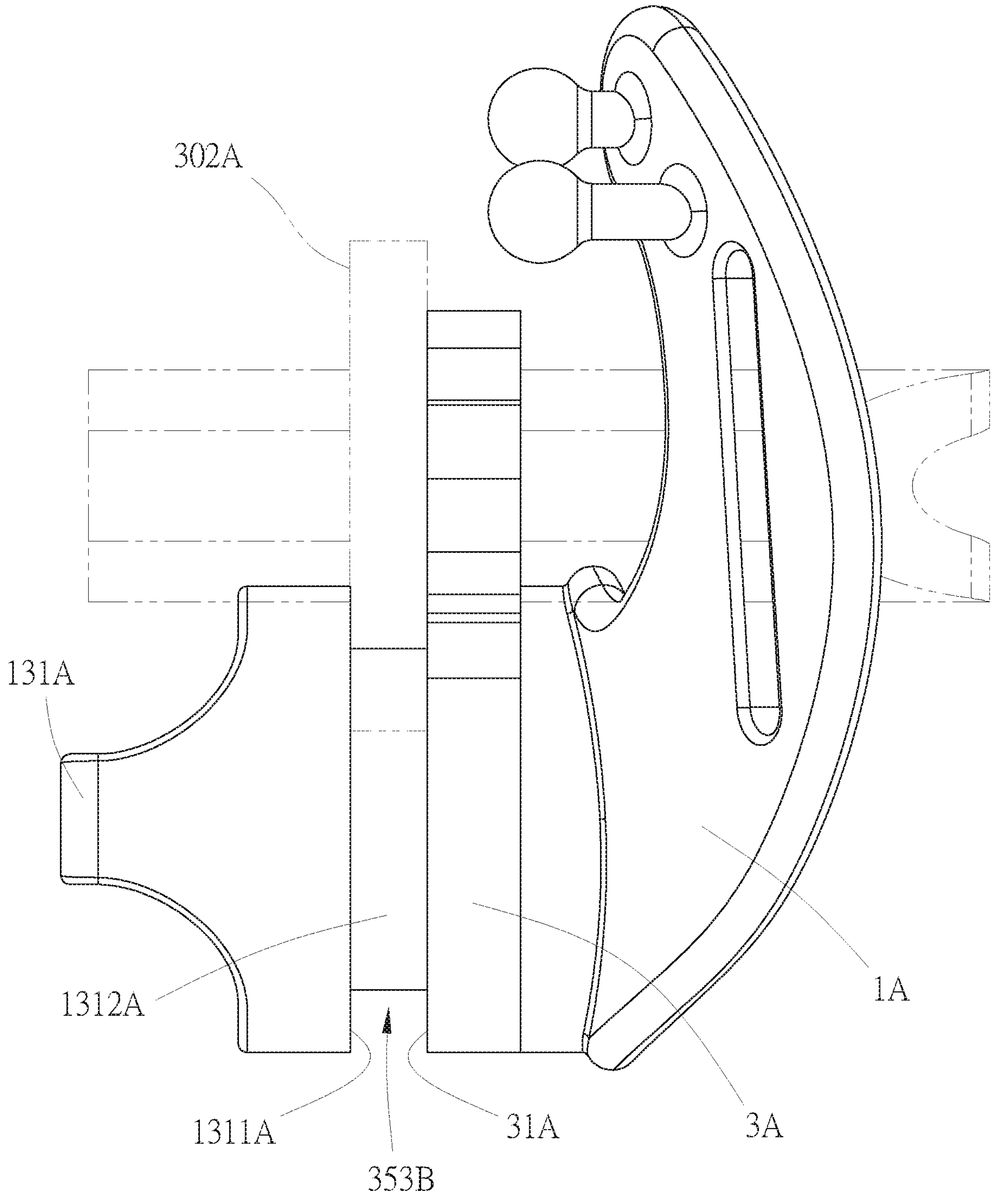
FIG. 24 is a side view of the fourth embodiment mounted with the bite block, wherein the holding portion of the bite block is engaged in the first holding groove.

After the sputum suction tube 4 is inserted through the endotracheal tube 10 to suck the sputum from the lungs and respiratory tract of the patient, the sputum suction tube 4 is inserted in the oral cavity 5 of the patient to suck the expectoration in the oral cavity 5. Please refer to FIG. 17, FIG. 18 and FIG. 19. The bite block 30 is removed first. Next, similar to the first embodiment, the movable cap 131 is unscrewed to be in the unlocking position, and the retaining seat 3 is rotated to the right or the left relative to the main body 1, so as to change the position of the retaining seat 3. As shown in FIG. 18, when the endotracheal tube 10 is retained by the first tube retaining portion 34, the retaining seat 3 is rotated to the right relative to the main body 1, and then the movable cap 131 is screwed to be in the locking position for retaining the retaining seat 3. As shown in FIG. 19, when the endotracheal tube 10 is retained by the second tube retaining portion 36, the retaining seat 3 is rotated to the left relative to the main body 1, and then the movable cap 131 is screwed to be in the locking position for retaining the retaining seat 3. Through the above operations, the sputum suction tube 4 can be inserted in the oral cavity 5 of the patient via the space of the open portion 12 to suck the expectoration in the oral cavity 5, without detaching the retaining seat 3 from the main body 1. Of course, a toothbrush may be inserted in the oral cavity 5 of the patient via the space of the open portion 12 to brush the patient's teeth.

The embodiment shown in FIG. 16 to FIG. 19 may further include a main body third tube retaining portion and a main body fourth tube retaining portion as shown in FIG. 4A, for retaining the orogastric tube.

Please refer to FIG. 20, FIG. 21, FIG. 22 and FIG. 23. In the fourth embodiment, compared with the above-mentioned second and third embodiments, the bite block 30A is held by the bite block holder 35A in a different way. The bite block retaining seat 35A has an opening 351A that is circular, and does not have the stopper 352 in the second and third embodiments (referring to FIG. 8). Specifically, a retaining seat 3A is connected to a main body 1A through a movable cap 131A. The movable cap 131A has an inner end face 1311A and a collar 1312A protruding from the inner end face 1311A. When in a locking position, the first face 31A, the collar 1312A and the inner end face 1311A jointly define a first holding groove 353B. The bite block 30A includes a bite portion 301A and a holding portion 302A surrounding the around bite portion 301A. The outer diameter of the holding portion 302A is greater than the outer diameter of the bite portion 301A. The thickness of the holding portion 302A corresponds to the groove width of the first holding groove 353B. The groove width refers to the linear distance between the inner end face 1311A and the first face 31A. The holding portion 302A has a notch 303A. The notch 303A corresponds in shape to a part of the periphery of the movable cap 131A. In this embodiment, the periphery of the movable cap 131A is circular, and the notch 303A is arc-shaped.

When the bite portion 301A is inserted into the opening 351A, the notch 303A is aligned with the position of the movable cap 131A, and the holding portion 302A passes through the periphery of the movable cap 131A and abuts against the first face 31A, and the holding portion 302A is rotated to be engaged in the first holding groove 353B, so that the bite block 30A is held by the bite block holder 35A.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A retaining device for medical equipment, comprising:

a main body including a solid portion, an open portion and a coupling unit, the open portion adapted to correspond in position to a mouth of a human body, the coupling unit being disposed on the solid portion, two sides of the main body being defined as a first side and a second side relative to a longitudinal centerline, respectively;

a strap coupled to the main body; and a retaining seat detachably and rotatably coupled to the solid portion through the coupling unit, the retaining seat including a first tube retaining portion, the first tube retaining portion corresponding in position to the open portion, the coupling unit including a movable cap and a protruding shaft, the retaining seat having a through hole, the retaining seat being sleeved on the protruding shaft via the through hole, the movable cap being coupled to the protruding shaft to form an unlocking position and a locking position, wherein, when in the unlocking position, the retaining seat is detachable from the solid portion to be reversed and rotatable relative to the main body, the retaining seat further including a bite block holder, the first tube retaining portion and the bite block holder being arranged along a transverse direction;

wherein a relative position between the first tube retaining portion and the open portion of the main body is adjustable by (a) detaching and reversing the retaining seat relative the solid portion of the main body and (b) rotating the retaining seat relative to the solid of the main body, whereby when the retaining device is worn and used by a patient and when the patient is in an upright position, the open portion of the main body is positioned above the protruding shaft and a through hole of the solid portion that receives the protruding shaft.

2. The retaining device as claimed in claim 1, wherein the coupling unit is located at a position where the longitudinal centerline passes, and the first tube retaining portion deviates from the longitudinal centerline.

3. The retaining device as claimed in claim 1, wherein the main body further includes a main body first tube retaining portion and a main body second tube retaining portion, wherein the main body first tube retaining portion is located on the first side of the main body, and the main body second tube retaining portion is located on a side of the main body selected from a group consisting of the first side and the second side.

4. The retaining device as claimed in claim 3, wherein the main body first tube retaining portion includes two first protruding posts, each first protruding post having a first enlarged end, and wherein a spacing between the first enlarged ends of the two first protruding posts is less than a spacing between the two first protruding posts; wherein the main body second tube retaining portion includes two second protruding posts, each having a second enlarged end, and wherein a spacing between the second enlarged ends of the two second protruding posts is less than a spacing between the two second protruding posts.

5. The retaining device as claimed in claim 4, wherein the main body further includes a main body third tube retaining portion and a main body fourth tube retaining portion, and wherein each of the main body third tube retaining portion and the main body fourth tube retaining portion is located on a side of the main body selected from a group consisting of the first side and the second side.

6. The retaining device as claimed in claim 5, wherein the main body third tube retaining portion includes two third protruding posts, each third protruding post having a third enlarged end, and wherein a spacing between the third enlarged ends of the two third protruding posts is less than a spacing between the two third protruding posts; wherein the main body fourth tube retaining portion includes two fourth protruding posts, each fourth protruding post having a fourth enlarged end, and wherein a spacing between the fourth enlarged ends of the two fourth protruding posts is less than a spacing between the two fourth protruding posts.

7. The retaining device as claimed in claim 1, wherein the retaining seat further includes a first face, wherein the bite block holder includes an opening, the movable cap has an inner end face and a collar protruding from the inner end face, when in the locking position, the first face, the collar and the inner end face jointly define a first holding groove; wherein the retaining device further comprises a bite block, the bite block including a bite portion and a holding portion surrounding the bite portion, wherein the holding portion has a thickness corresponding to a groove width of the first holding groove, and wherein the holding portion has a notch corresponding in shape to a part of a periphery of the movable cap.

* * * * *